(12) United States Patent
Wei et al.

(10) Patent No.: US 8,685,939 B2
(45) Date of Patent: Apr. 1, 2014

(54) VACCINE TARGETING CELLULAR DEATH RECEPTOR DR5

(75) Inventors: Wei-Zen Wei, Grosse Pointe Farms, MI (US); Gen Sheng Wu, Troy, MI (US); Marie P. Piechocki, Fraser, MI (US); Richard F. Jones, Fayetteville, NY (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 13/128,046

(22) PCT Filed: Nov. 6, 2009

(86) PCT No.: PCT/US2009/063499
§ 371 (c)(1),
(2), (4) Date: May 6, 2011

(87) PCT Pub. No.: WO2010/054156
PCT Pub. Date: May 14, 2010

(65) Prior Publication Data
US 2012/0189572 A1     Jul. 26, 2012

Related U.S. Application Data

(60) Provisional application No. 61/111,798, filed on Nov. 6, 2008.

(51) Int. Cl.
*A61K 45/00* (2006.01)
*A61K 31/00* (2006.01)
*A61K 39/395* (2006.01)

(52) U.S. Cl.
USPC .................. 514/44 R; 424/192.1; 424/278.1; 536/23.4; 530/387.3; 530/388.22; 530/389.7; 435/320.1

(58) Field of Classification Search
None
See application file for complete search history.

(56) References Cited

U.S. PATENT DOCUMENTS 7,897,730 B2 *  3/2011  Yu et al.

OTHER PUBLICATIONS

Lavrik et al., Death receptor signaling, J. Cell Sci. 118:265-267, 2005.*
Henson et al., The role of TRAIL death receptors in the treatment of hematological malignancies, Leukemia and Lymphoma, 49(1):27-35, Jan. 2008.*
King et al., DNA vaccines with single-chain Fv fused to fragment C of tetanus toxin induced protective immunity against lymphoma and myeloma, Nat. Med. 4(11):1281-1286, Nov. 1998.*
Chattergoon et al., DR5 activation of caspase-8 induces DC maturation and immune enhancement in vivo, Mol. Ther. 16(2):419-426, Feb. 2008, published online Dec. 18, 2007.*
Srinivasan et al., Tumor antigens for cancer immunotherapy: therapeutic potential of xenogenic DNA vaccines, J. Translational Med. 2:12, Apr. 16, 2004.*

(Continued)

*Primary Examiner* — Claire Kaufman
(74) *Attorney, Agent, or Firm* — Kohn & Associates, PLLC

(57) ABSTRACT

The invention provides therapeutics and methods to induce a mammalian host, including a human, to produce antibodies, which agonize death receptors and cause the apoptotic death of target cells within the host's body. The therapeutics are vaccine compositions, including genetic vaccines encoding death receptor antigens of the tumor necrosis factor receptor family. Also provided are means and methods for overcoming host immunological tolerance to death receptors. The vaccines are useful against cancer cells and other death receptor bearing target cells within the host, and can be used in both therapeutic and prophylactic settings. The vaccines are also useful for diagnostic testing of the immunocompetence of a host.

10 Claims, 15 Drawing Sheets

(56) References Cited

OTHER PUBLICATIONS

Takeda et al., Targeting death-inducing receptors in cancer therapy, Oncogene, 26:3745-3757, 2007.*

Zou et al., Cytokines in the generation and maturation of dendritic cells: recent advances, Eur. Cytokine Network, 13(2):186-99, Jun. 2002.*

Dranoff et al. Vaccination with irradiated tumor cells engineered to secrete murine granulocyte-macrophage colony-stimulating factor stimulates potent, specific, and long-lasting atni-tumor immunity, Proc. Natl. Acad. Sci., USA, 90:3539-3543, 1993.*

Montgomery et al., Chapter 2: Plasmid DNA constructs for vaccines, DNA VaccinesLMethods and Protocols, Second Edition, Saltzman et al., Eds, Humana Press: New Jersey, 2006, pp. 11-22.*

Wildbaum et al., A targeted DNA vaccine encoding Fas ligand defines its dual role in the regulation of experimental autoimmune encephalomyelitis, J. Clin. Invest. 106:671-679, 2000.*

Back et al., Inhibition of tumor growth by DNA vaccines encoding TRAIL receptor DR5, Proc. Am. Assoc. Cancer Res., 99th AACR Ann. Meeting—Apr. 12-16, 2008, San Diego, CA, Abstract #2872, 2008.*

* cited by examiner

SEQUENCE LISTING

```
<160> NUMBER OF SEQ ID NOS: 32

<210> SEQ ID NO 1
<211> LENGTH: 384
<212> TYPE: DNA
<213> ORGANISM: Mus musculus

<400> SEQUENCE: 1
aacccagccc ataatcgtcc agctggccta cagcggccgg aggagagccc atcaagagga      60
ccctgtctag caggccagta cctgtcagaa gggaactgca agccttgcag agagggtatt     120
gactacacca gccattccaa ccattctctg gattcatgta ttctctgcac agtctgtaag     180
gaagataaag tcgtagaaac ccgatgcaac ataaccacaa atacggtgtg tcgatgcaaa     240
ccaggcacct ttgaagataa agactcccct gagatctgcc agtcatgctc taactgcact     300
gacggggaag aggaactgac ttcctgtacc cccagagaaa accggaagtg tgtctccaaa     360
acggcttggg catcttggca taag                                            384
```

```
<210> SEQ ID NO 2
<211> LENGTH: 128
<212> TYPE: PRT
<213> ORGANISM: Mus musculus

<400> SEQUENCE: 2

Asn Pro Ala His Asn Arg Pro Ala Gly Leu Gln Arg Pro Glu Glu Ser
1               5                   10                  15

Pro Ser Arg Gly Pro Cys Leu Ala Gly Gln Tyr Leu Ser Glu Gly Asn
            20                  25                  30

Cys Lys Pro Cys Arg Glu Gly Ile Asp Tyr Thr Ser His Ser Asn His
        35                  40                  45

Ser Leu Asp Ser Cys Ile Leu Cys Thr Val Cys Lys Glu Asp Lys Val
    50                  55                  60

Val Glu Thr Arg Cys Asn Ile Thr Thr Asn Thr Val Cys Arg Cys Lys
65                  70                  75                  80

Pro Gly Thr Phe Glu Asp Lys Asp Ser Pro Glu Ile Cys Gln Ser Cys
                85                  90                  95

Ser Asn Cys Thr Asp Gly Glu Glu Leu Thr Ser Cys Thr Pro Arg
            100                 105                 110

Glu Asn Arg Lys Cys Val Ser Lys Thr Ala Trp Ala Ser Trp His Lys
            115                 120                 125

<210> SEQ ID NO 3
<211> LENGTH: 63
<212> TYPE: DNA
<213> ORGANISM: Mus musculus

<400> SEQUENCE: 3
ctaggcctct ggataggact cctggttcca gtagtgctgc tgattggagc tctgcttgtc      60
tgg                                                                   63

<210> SEQ ID NO 4
<211> LENGTH: 21
<212> TYPE: PRT
<213> ORGANISM: Mus musculus

<400> SEQUENCE: 4

Leu Gly Leu Trp Ile Gly Leu Leu Val Pro Val Leu Leu Ile Gly
1               5                   10                  15

Ala Leu Leu Val Trp
            20

<210> SEQ ID NO 5
<211> LENGTH: 390
<212> TYPE: DNA
<213> ORGANISM: Homo sapiens

<400> SEQUENCE: 5
gctctgatca cccaacaaga cctagctccc cagcagagag cggccccaca acaaagagg       60 tccagcccct cagagggatt gtgtccacct ggacaccata tctcagaaga cggtagagat     120
tgcatctcct gcaaatatgg acaggactat agcactcact ggaatgacct cctttttctgc   180 ttgcgctgca ccaggtgtga ttcaggtgaa gtggagctaa gtccctgcac cacgaccaga    240
aacacagtgt gtcagtgcga agaaggcacc ttccgggaag aagattctcc tgagatgtgc    300
cggaagtgcc gcacagggtg tccagagggg atggtcaagg tcggtgattg tacaccctgg    360
agtgacatcg aatgtgtcca caaagaatca                                      390
```

<210> SEQ ID NO 6
<211> LENGTH: 130
<212> TYPE: PRT
<213> ORGANISM: Homo sapiens

<400> SEQUENCE: 6

```
Ala Leu Ile Thr Gln Gln Asp Leu Ala Pro Gln Gln Arg Ala Ala Pro
 1               5                  10                  15
Gln Gln Lys Arg Ser Ser Pro Ser Glu Gly Leu Cys Pro Pro Gly His
            20                  25                  30
His Ile Ser Glu Asp Gly Arg Asp Cys Ile Ser Cys Lys Tyr Gly Gln
        35                  40                  45
Asp Tyr Ser Thr His Trp Asn Asp Leu Leu Phe Cys Leu Arg Cys Thr
    50                  55                  60
Arg Cys Asp Ser Gly Glu Val Glu Leu Ser Pro Cys Thr Thr Thr Arg
65                  70                  75                  80
Asn Thr Val Cys Gln Cys Glu Glu Gly Thr Phe Arg Glu Glu Asp Ser
                85                  90                  95
Pro Glu Met Cys Arg Lys Cys Arg Thr Gly Cys Pro Arg Gly Met Val
            100                 105                 110
Lys Val Gly Asp Cys Thr Pro Trp Ser Asp Ile Glu Cys Val His Lys
        115                 120                 125
Glu Ser
    130
```

<210> SEQ ID NO 7
<211> LENGTH: 57
<212> TYPE: DNA
<213> ORGANISM: Homo sapiens

<400> SEQUENCE: 7

```
ggcatcatca taggagtcac agttgcagcc gtagtcttga ttgtggctgt gtttgtt      57
```

<210> SEQ ID NO 8
<211> LENGTH: 19
<212> TYPE: PRT
<213> ORGANISM: Homo sapiens

<400> SEQUENCE: 8

```
Gly Ile Ile Ile Gly Val Thr Val Ala Ala Val Leu Ile Val Ala
 1               5                  10                  15
Val Phe Val
```

<210> SEQ ID NO 9
<211> LENGTH: 669
<212> TYPE: DNA
<213> ORGANISM: Artificial Sequence
<220> FEATURE:
<223> OTHER INFORMATION: Hybrid Homo sapiens X Rattus norvegicus
<220> FEATURE:
<221> NAME/KEY: misc_feature
<222> LOCATION: (307)..(486)
<223> OTHER INFORMATION: rat sequence

<400> SEQUENCE: 9

```
atggaacaac ggggacagaa cgccccggcc gcttcggggg cccggaaaag gcacggccca      60
ggacccaggg aggcgcgggg agccaggcct gggctccggg tccccaagac ccttgtgctc     120
gttgtcgccg cggtcctgct gttggtctca gctgagtctg ctctgatcac ccaacaagac     180
ctagctcccc agcagagagc ggccccacaa caaaagaggt ccagcccctc agagggattg     240
```

```
tgtccacctg gacaccatat ctcagaagac ggtagagatt gcatctcctg caaatatgga      300
caggactaca ccagcggtcc caacgtcctg ccttcctgcc tttcctgcag ggtctgtaag      360
gaagataaag tcataaaaag ccgatgcgtc aaagctagaa acacagagtg tgagtgcaaa      420
ccaggcagct ttgaagataa agactcgact gagatctgcc agacatgctc taacgggtgt      480
cccagaggga tggtcaaggt cggtgattgt acaccctgga gtgacatcga atgtgtccac      540
aaagaatcag gcatcatcat aggagtcaca gttgcagccg tagtcttgat tgtggctgtg      600
tttgtttgca agtctttact gtggaagaaa gtccttcctt acctgaaagg catctgctca      660
ggtggaggc                                                              669

<210> SEQ ID NO 10
<211> LENGTH: 223
<212> TYPE: PRT
<213> ORGANISM: Artificial Sequence
<220> FEATURE:
<223> OTHER INFORMATION: Hybrid Homo sapiens X Rattus norvegicus

<400> SEQUENCE: 10

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Leu
            20                  25                  30

Arg Val Pro Lys Thr Leu Val Leu Val Val Ala Ala Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Thr Ser Gly Pro Asn Val Leu Pro Ser
            100                 105                 110

Cys Leu Ser Cys Arg Val Cys Lys Glu Asp Lys Val Ile Lys Ser Arg
        115                 120                 125

Cys Val Lys Ala Arg Asn Thr Glu Cys Glu Cys Lys Pro Gly Ser Phe
    130                 135                 140

Glu Asp Lys Asp Ser Thr Glu Ile Cys Gln Thr Cys Ser Asn Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Ile Ile Ile Gly Val Thr Val Ala
            180                 185                 190

Ala Val Val Leu Ile Val Ala Val Phe Val Cys Lys Ser Leu Leu Trp
        195                 200                 205

Lys Lys Val Leu Pro Tyr Leu Lys Gly Ile Cys Ser Gly Gly Gly
    210                 215                 220

<210> SEQ ID NO 11
<211> LENGTH: 663
<212> TYPE: DNA
<213> ORGANISM: Mus musculus

<400> SEQUENCE: 11
atggagcctc caggacccag cacgcccaca gcctctgccg ctgcccgggc agatcactac       60
accccaggcc tcggccact cccgaagcgc agacttctat atagctttgc gttgctgctt      120
```

```
gctgtgctac aggctgtctt tgttccagta acagctaacc cagcccataa tcgtccagct    180
ggcctacagc ggccggagga gagcccatca agaggaccct gtctagcagg ccagtacctg    240
tcagaaggga actgcaagcc ttgcagagag ggtattgact acaccagcca ttccaaccat    300
tctctggatt catgtattct ctgcacagtc tgtaaggaag ataaagtcgt agaaacccga    360
tgcaacataa ccacaaatac ggtgtgtcga tgcaaaccag gcacctttga agataaagac    420 tccccctgaga tctgccagtc atgctctaac tgcactgacg gggaagagga actgacttcc    480
tgtaccccca gagaaaaccg aagtgtgtc tccaaaacgg cttgggcatc ttggcataag    540
ctaggcctct ggataggact cctggttcca gtagtgctgc tgattggagc tctgcttgtc    600
tggaagactg gagcatggag gcaatggttg ctctgtataa aaagaggctg tgaacgggat    660
ccc                                                                  663

<210> SEQ ID NO 12
<211> LENGTH: 221
<212> TYPE: PRT
<213> ORGANISM: Mus musculus

<400> SEQUENCE: 12

Met Glu Pro Pro Gly Pro Ser Thr Pro Thr Ala Ser Ala Ala Ala Arg
1               5                   10                  15

Ala Asp His Tyr Thr Pro Gly Leu Arg Pro Leu Pro Lys Arg Arg Leu
            20                  25                  30

Leu Tyr Ser Phe Ala Leu Leu Leu Ala Val Leu Gln Ala Val Phe Val
        35                  40                  45

Pro Val Thr Ala Asn Pro Ala His Asn Arg Pro Ala Gly Leu Gln Arg
    50                  55                  60

Pro Glu Glu Ser Pro Ser Arg Gly Pro Cys Leu Ala Gly Gln Tyr Leu
65                  70                  75                  80

Ser Glu Gly Asn Cys Lys Pro Cys Arg Glu Gly Ile Asp Tyr Thr Ser
                85                  90                  95

His Ser Asn His Ser Leu Asp Ser Cys Ile Leu Cys Thr Val Cys Lys
            100                 105                 110

Glu Asp Lys Val Val Glu Thr Arg Cys Asn Ile Thr Thr Asn Thr Val
        115                 120                 125

Cys Arg Cys Lys Pro Gly Thr Phe Glu Asp Lys Asp Ser Pro Glu Ile
    130                 135                 140

Cys Gln Ser Cys Ser Asn Cys Thr Asp Gly Glu Glu Leu Thr Ser
145                 150                 155                 160

Cys Thr Pro Arg Glu Asn Arg Lys Cys Val Ser Lys Thr Ala Trp Ala
                165                 170                 175

Ser Trp His Lys Leu Gly Leu Trp Ile Gly Leu Val Pro Val Val
            180                 185                 190

Leu Leu Ile Gly Ala Leu Leu Val Trp Lys Thr Gly Ala Trp Arg Gln
        195                 200                 205

Trp Leu Leu Cys Ile Lys Arg Gly Cys Glu Arg Asp Pro
    210                 215                 220

<210> SEQ ID NO 13
<211> LENGTH: 669
<212> TYPE: DNA
<213> ORGANISM: Homo sapiens

<400> SEQUENCE: 13
atggaacaac ggggacagaa cgccccggcc gcttcggggg cccggaaaag gcacggccca    60
```

```
ggacccaggg aggcgcgggg agccaggcct gggctccggg tccccaagac ccttgtgctc    120
gttgtcgccg cggtcctgct gttggtctca gctgagtctg ctctgatcac ccaacaagac    180
ctagctcccc agcagagagc ggccccacaa caaagaggt ccagcccctc agagggattg     240
tgtccacctg gacaccatat ctcagaagac ggtagagatt gcatctcctg caaatatgga    300
caggactata gcactcactg gaatgacctc cttttctgct tgcgctgcac caggtgtgat    360
tcaggtgaag tggagctaag tccctgcacc acgaccagaa acacagtgtg tcagtgcgaa    420
gaaggcacct tccgggaaga agattctcct gagatgtgcc ggaagtgccg cacagggtgt    480
cccagaggga tggtcaaggt cggtgattgt cacccctgga gtgacatcga atgtgtccac    540
aaagaatcag gcatcatcat aggagtcaca gttgcagccg tagtcttgat tgtggctgtg    600
tttgtttgca gtctttact gtggaagaaa gtccttcctt acctgaaagg catctgctca    660
ggtggaggc                                                            669
```

<210> SEQ ID NO 14
<211> LENGTH: 223
<212> TYPE: PRT
<213> ORGANISM: Homo sapiens

<400> SEQUENCE: 14

```
Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Leu
            20                  25                  30

Arg Val Pro Lys Thr Leu Val Leu Val Val Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Ile Ile Ile Gly Val Thr Val Ala
            180                 185                 190

Ala Val Val Leu Ile Val Ala Val Phe Val Cys Lys Ser Leu Leu Trp
        195                 200                 205

Lys Lys Val Leu Pro Tyr Leu Lys Gly Ile Cys Ser Gly Gly Gly
    210                 215                 220
```

<210> SEQ ID NO 15
<211> LENGTH: 1449
<212> TYPE: DNA
<213> ORGANISM: Mus musculus

<400> SEQUENCE: 15

```
atggagcctc caggacccag cacgcccaca gcctctgccg ctgcccgggc agatcactac    60 acccccaggcc tccggccact cccgaagcgc agacttctat atagctttgc gttgctgctt   120
gctgtgctac aggctgtctt tgttccagta acagctaacc cagcccataa tcgtccagct   180
ggcctacagc ggccggagga gagcccatca agaggaccct gtctagcagg ccagtacctg   240
tcagaaggga actgcaagcc ttgcagagag ggtattgact acaccagcca ttccaaccat   300
tctctggatt catgtattct ctgcacagtc tgtaaggaag ataaagtcgt agaaacccga   360
tgcaacataa ccacaaatac ggtgtgtcga tgcaaaccag gcacctttga agataaagac   420 tccccctgaga tctgccagtc atgctctaac tgcactgacg gggaagagga actgacttcc   480
tgtaccccca gagaaaaccg gaagtgtgtc tccaaaacgg cttgggcatc ttggcataag   540
ctaggcctct ggataggact cctggttcca gtagtgctgc tgattggagc tctgcttgtc   600
tggaagactg gagcatggag gcaatggttg ctctgtataa aaagaggctg tgaacgggat   660
ccactagtcc agtgtggtgg aatggaaaac cttgattgtt gggtcgacaa cgaagaagac   720
atcgatgtta tcctgaaaaa gtctaccatt ctgaacttgg acatcaacaa cgatattatc   780
tccgacatct ctggttttcaa ctcctctgtt atcacatatc cagatgctca attggtgccg   840
ggcatcaacg gcaaagctat ccacctggtt aacaacgaat cttctgaagt tatcgtgcac   900
aaggccatgg acatcgaata acgacatg ttcaacaact tcaccgttag cttctggctg   960
cgcgttccga agtttctgc ttcccacctg aacagtacg gcactaacga gtactccatc  1020
atcagctcta tgaagaaaca ctccctgtcc atcggctctg gttggtctgt ttccctgaag  1080
ggtaacaacc tgatctggac tctgaaagac tccgcgggcg aagttcgtca gatcactttc  1140
cgcgacctgc cggacaagtt caacgcgtac ctggctaaca atgggttttt catcactatc  1200
actaacgatc gtctgtcttc tgctaacctg tacatcaacg gcgttctgat gggctccgct  1260
gaaatcactg gtctgggcgc tatccgtgag gacaacaaca tcactcttaa gctggaccgt  1320
tgcaacaaca caaccagta cgtatccatc gacaagttcc gtatcttctg caaagcactg  1380
aacccgaaag agatcgaaaa actgtatacc agctacctgt ctatcacctt cctgcgtgac  1440
ttctggggt                                                         1449
```

<210> SEQ ID NO 16
<211> LENGTH: 483
<212> TYPE: PRT
<213> ORGANISM: Mus musculus

<400> SEQUENCE: 16

```
Met Glu Pro Pro Gly Pro Ser Thr Pro Thr Ala Ser Ala Ala Ala Arg
1               5                   10                  15

Ala Asp His Tyr Thr Pro Gly Leu Arg Pro Leu Pro Lys Arg Arg Leu
            20                  25                  30

Leu Tyr Ser Phe Ala Leu Leu Leu Ala Val Leu Gln Ala Val Phe Val
        35                  40                  45

Pro Val Thr Ala Asn Pro Ala His Asn Arg Pro Ala Gly Leu Gln Arg
    50                  55                  60

Pro Glu Glu Ser Pro Ser Arg Gly Pro Cys Leu Ala Gly Gln Tyr Leu
65                  70                  75                  80

Ser Glu Gly Asn Cys Lys Pro Cys Arg Glu Gly Ile Asp Tyr Thr Ser
                85                  90                  95

His Ser Asn His Ser Leu Asp Ser Cys Ile Leu Cys Thr Val Cys Lys
            100                 105                 110

Glu Asp Lys Val Val Glu Thr Arg Cys Asn Ile Thr Thr Asn Thr Val
```

```
                115                 120                 125
Cys Arg Cys Lys Pro Gly Thr Phe Glu Asp Lys Asp Ser Pro Glu Ile
130                 135                 140

Cys Gln Ser Cys Ser Asn Cys Thr Asp Gly Glu Glu Leu Thr Ser
145                 150                 155                 160

Cys Thr Pro Arg Glu Asn Arg Lys Cys Val Ser Lys Thr Ala Trp Ala
                165                 170                 175

Ser Trp His Lys Leu Gly Leu Trp Ile Gly Leu Leu Val Pro Val Val
            180                 185                 190

Leu Leu Ile Gly Ala Leu Leu Val Trp Lys Thr Gly Ala Trp Arg Gln
            195                 200                 205

Trp Leu Leu Cys Ile Lys Arg Gly Cys Glu Arg Asp Pro Leu Val Gln
        210                 215                 220

Cys Gly Gly Met Glu Asn Leu Asp Cys Trp Val Asp Asn Glu Glu Asp
225                 230                 235                 240

Ile Asp Val Ile Leu Lys Lys Ser Thr Ile Leu Asn Leu Asp Ile Asn
                245                 250                 255

Asn Asp Ile Ile Ser Asp Ile Ser Gly Phe Asn Ser Ser Val Ile Thr
            260                 265                 270

Tyr Pro Asp Ala Gln Leu Val Pro Gly Ile Asn Gly Lys Ala Ile His
        275                 280                 285

Leu Val Asn Asn Glu Ser Ser Glu Val Ile Val His Lys Ala Met Asp
    290                 295                 300

Ile Glu Tyr Asn Asp Met Phe Asn Asn Phe Thr Val Ser Phe Trp Leu
305                 310                 315                 320

Arg Val Pro Lys Val Ser Ala Ser His Leu Glu Gln Tyr Gly Thr Asn
                325                 330                 335

Glu Tyr Ser Ile Ile Ser Ser Met Lys Lys His Ser Leu Ser Ile Gly
            340                 345                 350

Ser Gly Trp Ser Val Ser Leu Lys Gly Asn Asn Leu Ile Trp Thr Leu
        355                 360                 365

Lys Asp Ser Ala Gly Glu Val Arg Gln Ile Thr Phe Arg Asp Leu Pro
370                 375                 380

Asp Lys Phe Asn Ala Tyr Leu Ala Asn Lys Trp Val Phe Ile Thr Ile
385                 390                 395                 400

Thr Asn Asp Arg Leu Ser Ser Ala Asn Leu Tyr Ile Asn Gly Val Leu
                405                 410                 415

Met Gly Ser Ala Glu Ile Thr Gly Leu Gly Ala Ile Arg Glu Asp Asn
            420                 425                 430

Asn Ile Thr Leu Lys Leu Asp Arg Cys Asn Asn Asn Gln Tyr Val
        435                 440                 445

Ser Ile Asp Lys Phe Arg Ile Phe Cys Lys Ala Leu Asn Pro Lys Glu
    450                 455                 460

Ile Glu Lys Leu Tyr Thr Ser Tyr Leu Ser Ile Thr Phe Leu Arg Asp
465                 470                 475                 480

Phe Trp Gly

<210> SEQ ID NO 17
<211> LENGTH: 1412
<212> TYPE: DNA
<213> ORGANISM: Mus musculus
<220> FEATURE:
<221> NAME/KEY: misc_feature
<222> LOCATION: (1)..(663)
<223> OTHER INFORMATION: mDR5ectm w/signal peptide
<220> FEATURE:
```

```
<221> NAME/KEY: misc_feature
<222> LOCATION: (693)..(1412)
<223> OTHER INFORMATION: eGFP

<400> SEQUENCE: 17
atggagcctc caggacccag cacgcccaca gcctctgccg ctgcccgggc agatcactac      60
accccaggcc tccggccact cccgaagcgc agacttctat atagctttgc gttgctgctt     120
gctgtgctac aggctgtctt tgttccagta acagctaacc cagcccataa tcgtccagct     180
ggcctacagc ggccggagga gagcccatca agaggaccct gtctagcagg ccagtacctg     240
tcagaaggga actgcaagcc ttgcagagag ggtattgact acaccagcca ttccaaccat     300
tctctggatt catgtattct ctgcacagtc tgtaaggaag ataaagtcgt agaaacccga     360
tgcaacataa ccacaaatac ggtgtgtcga tgcaaccag gcacctttga agataaagac       420
tcccctgaga tctgccagtc atgctctaac tgcactgacg gggaagagga actgacttcc     480
tgtaccccca gagaaaaccg gaagtgtgtc tccaaaacgg cttgggcatc ttggcataag     540
ctaggcctct ggataggact cctggttcca gtagtgctgc tgattggagc tctgcttgtc     600
tggaagactg gagcatggag gcaatggttg ctctgtataa aaagaggctg tgaacgggat     660
cggtgaccgc ggtcaccgat ccaccggtcg ccaccatggt gagcaagggc gaggagctgt     720
tcaccggggt ggtgcccatc ctggtcgagc tggacggcga cgtaaacggc cacaagttca     780
gcgtgtccgg cgagggcgag ggcgatgcca cctacggcaa gctgaccctg aagttcatct     840
gcaccaccgg caagctgccc gtgccctggc ccaccctcgt gaccaccctg acctacggcg     900
tgcagtgctt cagccgctac cccgaccaca tgaagcagca cgacttcttc aagtccgcca     960
tgcccgaagg ctacgtccag gagcgcacca tcttcttcaa ggacgacggc aactacaaga    1020
cccgcgccga ggtgaagttc gagggcgaca ccctggtgaa ccgcatcgag ctgaagggca    1080
tcgacttcaa ggaggacggc aacatcctgg ggcacaagct ggagtacaac tacaacagcc    1140
acaacgtcta tatcatggcc gacaagcaga agaacggcat caaggtgaac ttcaagatcc    1200
gccacaacat cgaggacggc agcgtgcagc tcgccgacca ctaccagcag aacaccccca    1260
tcggcgacgg ccccgtgctg ctgcccgaca accactacct gagcacccag tccgccctga    1320
gcaaagaccc caacgagaag cgcgatcaca tggtcctgct ggagttcgtg accgccgccg    1380
ggatcactct cggcatggac gagctgtaca ag                                  1412

<210> SEQ ID NO 18
<211> LENGTH: 460
<212> TYPE: PRT
<213> ORGANISM: Mus musculus
<220> FEATURE:
<221> NAME/KEY: PEPTIDE
<222> LOCATION: (1)..(221)
<223> OTHER INFORMATION: mDR5ectm
<220> FEATURE:
<221> NAME/KEY: PEPTIDE
<222> LOCATION: (222)..(460)
<223> OTHER INFORMATION: eGFP

<400> SEQUENCE: 18

Met Glu Pro Pro Gly Pro Ser Thr Pro Thr Ala Ser Ala Ala Ala Arg
1               5                   10                  15

Ala Asp His Tyr Thr Pro Gly Leu Arg Pro Leu Pro Lys Arg Arg Leu
                20                  25                  30

Leu Tyr Ser Phe Ala Leu Leu Leu Ala Val Leu Gln Ala Val Phe Val
            35                  40                  45

Pro Val Thr Ala Asn Pro Ala His Asn Arg Pro Ala Gly Leu Gln Arg
```

```
                50                  55                  60
Pro Glu Glu Ser Pro Ser Arg Gly Pro Cys Leu Ala Gly Gln Tyr Leu
 65                  70                  75                  80

Ser Glu Gly Asn Cys Lys Pro Cys Arg Glu Gly Ile Asp Tyr Thr Ser
                 85                  90                  95

His Ser Asn His Ser Leu Asp Ser Cys Ile Leu Cys Thr Val Cys Lys
                100                 105                 110

Glu Asp Lys Val Val Glu Thr Arg Cys Asn Ile Thr Thr Asn Thr Val
            115                 120                 125

Cys Arg Cys Lys Pro Gly Thr Phe Glu Asp Lys Asp Ser Pro Glu Ile
130                 135                 140

Cys Gln Ser Cys Ser Asn Cys Thr Asp Gly Glu Glu Glu Leu Thr Ser
145                 150                 155                 160

Cys Thr Pro Arg Glu Asn Arg Lys Cys Val Ser Lys Thr Ala Trp Ala
                165                 170                 175

Ser Trp His Lys Leu Gly Leu Trp Ile Gly Leu Leu Val Pro Val Val
                180                 185                 190

Leu Leu Ile Gly Ala Leu Leu Val Trp Lys Thr Gly Ala Trp Arg Gln
            195                 200                 205

Trp Leu Leu Cys Ile Lys Arg Gly Cys Glu Arg Asp Arg Met Val Ser
210                 215                 220

Lys Gly Glu Glu Leu Phe Thr Gly Val Val Pro Ile Leu Val Glu Leu
225                 230                 235                 240

Asp Gly Asp Val Asn Gly His Lys Phe Ser Val Ser Gly Glu Gly Glu
                245                 250                 255

Gly Asp Ala Thr Tyr Gly Lys Leu Thr Leu Lys Phe Ile Cys Thr Thr
            260                 265                 270

Gly Lys Leu Pro Val Pro Trp Pro Thr Leu Val Thr Thr Leu Thr Tyr
        275                 280                 285

Gly Val Gln Cys Phe Ser Arg Tyr Pro Asp His Met Lys Gln His Asp
        290                 295                 300

Phe Phe Lys Ser Ala Met Pro Glu Gly Tyr Val Gln Glu Arg Thr Ile
305                 310                 315                 320

Phe Phe Lys Asp Asp Gly Asn Tyr Lys Thr Arg Ala Glu Val Lys Phe
                325                 330                 335

Glu Gly Asp Thr Leu Val Asn Arg Ile Glu Leu Lys Gly Ile Asp Phe
            340                 345                 350

Lys Glu Asp Gly Asn Ile Leu Gly His Lys Leu Glu Tyr Asn Tyr Asn
        355                 360                 365

Ser His Asn Val Tyr Ile Met Ala Asp Lys Gln Lys Asn Gly Ile Lys
    370                 375                 380

Val Asn Phe Lys Ile Arg His Asn Ile Glu Asp Gly Ser Val Gln Leu
385                 390                 395                 400

Ala Asp His Tyr Gln Gln Asn Thr Pro Ile Gly Asp Gly Pro Val Leu
                405                 410                 415

Leu Pro Asp Asn His Tyr Leu Ser Thr Gln Ser Ala Leu Ser Lys Asp
            420                 425                 430

Pro Asn Glu Lys Arg Asp His Met Val Leu Leu Glu Phe Val Thr Ala
        435                 440                 445

Ala Gly Ile Thr Leu Gly Met Asp Glu Leu Tyr Lys
        450                 455                 460

<210> SEQ ID NO 19
<211> LENGTH: 660
```

-continued

```
<212> TYPE: DNA
<213> ORGANISM: Artificial Sequence
<220> FEATURE:
<223> OTHER INFORMATION: Hybrid Homo sapiens X Rattus norvegicus
<220> FEATURE:
<221> NAME/KEY: misc_feature
<222> LOCATION: (280)..(444)
<223> OTHER INFORMATION: Rat sequence

<400> SEQUENCE: 19
atggagcctc caggacccag cacgcccaca gcctctgccg ctgcccgggc agatcactac    60
accccaggcc tccggccact cccgaagcgc agacttctat atagctttgc gttgctgctt   120
gctatgctac aggctgtctt tgttccagta acagctaacc cagcccataa tcgtccagct   180
ggcctacagc ggccggagga gagcccatca gaggaccct gtctagcagg ccagtacctg   240
tcagaaggga actgcaagcc ttgcagagag ggtattgact acaccagcgg tcccaacgtc   300
ctgccttcct gcctttcctg cagggtctgt aaggaagata agtcataaa aagccgatgc   360 gtcaaagcta gaaacacaga gtgtgagtgc aaaccaggca gctttgaaga taaagactcg   420
actgagatct gccagacatg ctctaactgc actgacgggg aagaggaact gacttcctgt   480
acccccagag aaaaccggaa gtgtgtctcc aaaacggctt gggcatcttg cataagcta   540 ggcctctgga taggactcct ggttccagta gtgctgctga ttggagctct gcttgtctgg   600
aagactggag catggaggca atggttgctc tgtataaaaa gaggctgtga acgggatcca   660

<210> SEQ ID NO 20
<211> LENGTH: 220
<212> TYPE: PRT
<213> ORGANISM: Artificial Sequence
<220> FEATURE:
<223> OTHER INFORMATION: Hybrid Homo sapiens X Rattus norvegicus

<400> SEQUENCE: 20

Met Glu Pro Pro Gly Pro Ser Thr Pro Thr Ala Ser Ala Ala Ala Arg
1               5                   10                  15

Ala Asp His Tyr Thr Pro Gly Leu Arg Pro Leu Pro Lys Arg Arg Leu
                20                  25                  30

Leu Tyr Ser Phe Ala Leu Leu Leu Ala Met Leu Gln Ala Val Phe Val
            35                  40                  45

Pro Val Thr Ala Asn Pro Ala His Asn Arg Pro Ala Gly Leu Gln Arg
        50                  55                  60

Pro Glu Glu Ser Pro Ser Arg Gly Pro Cys Leu Ala Gly Gln Tyr Leu
65                  70                  75                  80

Ser Glu Gly Asn Cys Lys Pro Cys Arg Glu Gly Ile Asp Tyr Thr Ser
                85                  90                  95

Gly Pro Asn Val Leu Pro Ser Cys Leu Ser Cys Arg Val Cys Lys Glu
            100                 105                 110

Asp Lys Val Ile Lys Ser Arg Cys Val Lys Ala Arg Asn Thr Glu Cys
        115                 120                 125

Glu Cys Lys Pro Gly Ser Phe Glu Asp Lys Asp Ser Thr Glu Ile Cys
    130                 135                 140

Gln Thr Cys Ser Asn Cys Thr Asp Gly Glu Glu Leu Thr Ser Cys
145                 150                 155                 160

Thr Pro Arg Glu Asn Arg Lys Cys Val Ser Lys Thr Ala Trp Ala Ser
                165                 170                 175

Trp His Lys Leu Gly Leu Trp Ile Gly Leu Leu Val Pro Val Val Leu
            180                 185                 190

Leu Ile Gly Ala Leu Leu Val Trp Lys Thr Gly Ala Trp Arg Gln Trp
```

Leu Leu Cys Ile Lys Arg Gly Cys Glu Arg Asp Pro
    210             215                 220

<210> SEQ ID NO 21
<211> LENGTH: 1233
<212> TYPE: DNA
<213> ORGANISM: Homo sapiens

<400> SEQUENCE: 21
atggaacaac ggggacagaa cgccccggcc gcttcggggg cccggaaaag gcacggccca      60
ggacccaggg aggcgcgggg agccaggcct gggctccggg tccccaagac ccttgtgctc     120
gttgtcgccg cggtcctgct gttggtctca gctgagtctg ctctgatcac ccaacaagac     180
ctagctcccc agcagagagc ggcccacaa caaaagaggt ccagcccctc agagggattg      240
tgtccacctg gacaccatat ctcagaagac ggtagagatt gcatctcctg caaatatgga     300
caggactata gcactcactg gaatgacctc cttttctgct gcgctgcac caggtgtgat      360
tcaggtgaag tggagctaag tccctgcacc acgaccagaa acacagtgtg tcagtgcgaa     420
gaaggcacct tccgggaaga agattctcct gagatgtgcc ggaagtgccg cacagggtgt     480
cccagaggga tggtcaaggt cggtgattgt acaccctgga gtgacatcga atgtgtccac     540
aaagaatcag gcatcatcat aggagtcaca gttgcagccg tagtcttgat gtggctgtg      600
tttgtttgca agtctttact gtggaagaaa gtccttcctt acctgaaagg catctgctca     660
ggtggaggcg ggaccctga gcgtgtggac agaagctcac aacgacctgg ggctgaggac      720
aatgtcctca tgagatcgt gagtatcttg cagcccaccc aggtccctga gcaggaaatg     780
gaagtccagg agccagcaga gccaacaggt gtcaacatgt tgtcccccgg ggagtcagag     840
catctgctgg aaccggcaga agctgaaagg tctcagagga ggaggctgct ggttccagca     900
aatgaaggtg atccccactga gactctgaga cagtgcttcg atgactttgc agacttggtg     960
cccttttgact cctgggagcc gctcatgagg aagttgggcc tcatggacaa tgagataaag    1020
gtggctaaag ctgaggcagc gggccacagg gacaccttgt acacgatgct gataaagtgg    1080
gtcaacaaaa ccgggcgaga tgcctctgtc cacaccctgc tggatgcctt ggagacgctg    1140
ggagagagac ttgccaagca gaagattgag gaccacttgt tgagctctgg aaagttcatg    1200
tatctagaag gtaatgcaga ctctgccatg tcc                                 1233

<210> SEQ ID NO 22
<211> LENGTH: 411
<212> TYPE: PRT
<213> ORGANISM: Homo sapiens

<400> SEQUENCE: 22

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Leu
                20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
        50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

```
Cys Lys Tyr Gly Gln Asp Tyr Ser Thr His Trp Asn Asp Leu Leu Phe
            100                 105                 110
Cys Leu Arg Cys Thr Arg Cys Asp Ser Gly Glu Val Glu Leu Ser Pro
            115                 120                 125
Cys Thr Thr Thr Arg Asn Thr Val Cys Gln Cys Glu Glu Gly Thr Phe
        130                 135                 140
Arg Glu Glu Asp Ser Pro Glu Met Cys Arg Lys Cys Arg Thr Gly Cys
145                 150                 155                 160
Pro Arg Gly Met Val Lys Val Gly Asp Cys Thr Pro Trp Ser Asp Ile
                165                 170                 175
Glu Cys Val His Lys Glu Ser Gly Ile Ile Ile Gly Val Thr Val Ala
                180                 185                 190
Ala Val Val Leu Ile Val Ala Val Phe Val Cys Lys Ser Leu Leu Trp
            195                 200                 205
Lys Lys Val Leu Pro Tyr Leu Lys Gly Ile Cys Ser Gly Gly Gly Gly
        210                 215                 220
Asp Pro Glu Arg Val Asp Arg Ser Ser Gln Arg Pro Gly Ala Glu Asp
225                 230                 235                 240
Asn Val Leu Asn Glu Ile Val Ser Ile Leu Gln Pro Thr Gln Val Pro
                245                 250                 255
Glu Gln Glu Met Glu Val Gln Glu Pro Ala Glu Pro Thr Gly Val Asn
                260                 265                 270
Met Leu Ser Pro Gly Glu Ser Glu His Leu Leu Glu Pro Ala Glu Ala
            275                 280                 285
Glu Arg Ser Gln Arg Arg Arg Leu Leu Val Pro Ala Asn Glu Gly Asp
        290                 295                 300
Pro Thr Glu Thr Leu Arg Gln Cys Phe Asp Asp Phe Ala Asp Leu Val
305                 310                 315                 320
Pro Phe Asp Ser Trp Glu Pro Leu Met Arg Lys Leu Gly Leu Met Asp
                325                 330                 335
Asn Glu Ile Lys Val Ala Lys Ala Glu Ala Ala Gly His Arg Asp Thr
                340                 345                 350
Leu Tyr Thr Met Leu Ile Lys Trp Val Asn Lys Thr Gly Arg Asp Ala
            355                 360                 365
Ser Val His Thr Leu Leu Asp Ala Leu Glu Thr Leu Gly Glu Arg Leu
        370                 375                 380
Ala Lys Gln Lys Ile Glu Asp His Leu Leu Ser Ser Gly Lys Phe Met
385                 390                 395                 400
Tyr Leu Glu Gly Asn Ala Asp Ser Ala Met Ser
                405                 410

<210> SEQ ID NO 23
<211> LENGTH: 1443
<212> TYPE: DNA
<213> ORGANISM: Homo sapiens

<400> SEQUENCE: 23
atggaacaac ggggacagaa cgccccggcc gcttcggggg cccggaaaag gcacggccca      60
ggacccaggg aggcgcgggg agccaggcct gggccccggg tccccaagac ccttgtgctc     120
gttgtcgccg cggtcctgct gttggtctca gctgagtctg ctctgatcac ccaacaagac     180
ctagctcccc agcagagagc ggccccacaa caaagaggt ccagcccctc agagggattg      240
tgtccacctg acaccatat ctcagaagac ggtagagatt gcatctcctg caaatatgga      300
caggactata gcactcactg gaatgacctc cttttctgct tgcgctgcac caggtgtgat      360
```

```
tcaggtgaag tggagctaag tccctgcacc acgaccagaa acacagtgtg tcagtgcgaa    420
gaaggcacct tccgggaaga agattctcct gagatgtgcc ggaagtgccg cacagggtgt    480
cccagaggga tggtcaaggt cggtgattgt acaccctgga gtgacatcga atgtgtccac    540
aaagaatcag gcatcatcat aggagtcaca gttgcagccg tagtcttgat tgtggctgtg    600
tttgtttgca agtctttact gtggaagaaa gtccttcctt acctgaaagg catctgctca    660
ggtggaggca aaaaccttga ttgttgggtc gacaacgaag aagacatcga tgttatcctg    720
aaaaagtcta ccattctgaa cttggacatc aacaacgata ttatctccga catctctggt    780
ttcaactcct ctgttatcac atatccagat gctcaattgg tgccgggcat caacggcaaa    840
gctatccacc tggttaacaa cgaatcttct gaagttatcg tgcacaaggc catggacatc    900
gaatacaacg acatgttcaa caacttcacc gttagcttct ggctgcgcgt tccgaaagtt    960
tctgcttccc acctggaaca gtacggcact aacgagtact ccatcatcag ctctatgaag   1020
aaacactccc tgtccatcgg ctctggttgg tctgtttccc tgaagggtaa caacctgatc   1080
tggactctga aagactccgc gggcgaagtt cgtcagatca ctttccgcga cctgccggac   1140
aagttcaacg cgtacctggc taacaaatgg gttttcatca ctatcactaa cgatcgtctg   1200
tcttctgcta acctgtacat caacggcgtt ctgatgggct ccgctgaaat cactggtctg   1260
ggcgctatcc gtgaggacaa caacatcact cttaagctgg accgttgcaa caacaacaac   1320
cagtacgtat ccatcgacaa gttccgtatc ttctgcaaag cactgaaccc gaaagagatc   1380
gaaaaactgt ataccagcta cctgtctatc accttcctgc gtgacttctg gggtaacccg   1440
ctg                                                                 1443

<210> SEQ ID NO 24
<211> LENGTH: 481
<212> TYPE: PRT
<213> ORGANISM: Homo sapiens

<400> SEQUENCE: 24

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175
```

-continued

```
Glu Cys Val His Lys Glu Ser Gly Ile Ile Ile Gly Val Thr Val Ala
                180                 185                 190
Ala Val Val Leu Ile Val Ala Val Phe Val Cys Lys Ser Leu Leu Trp
            195                 200                 205
Lys Lys Val Leu Pro Tyr Leu Lys Gly Ile Cys Ser Gly Gly Lys
210                 215                 220
Asn Leu Asp Cys Trp Val Asp Asn Glu Glu Asp Ile Asp Val Ile Leu
225                 230                 235                 240
Lys Lys Ser Thr Ile Leu Asn Leu Asp Ile Asn Asn Asp Ile Ile Ser
                245                 250                 255
Asp Ile Ser Gly Phe Asn Ser Ser Val Ile Thr Tyr Pro Asp Ala Gln
                260                 265                 270
Leu Val Pro Gly Ile Asn Gly Lys Ala Ile His Leu Val Asn Asn Glu
            275                 280                 285
Ser Ser Glu Val Ile Val His Lys Ala Met Asp Ile Glu Tyr Asn Asp
290                 295                 300
Met Phe Asn Asn Phe Thr Val Ser Phe Trp Leu Arg Val Pro Lys Val
305                 310                 315                 320
Ser Ala Ser His Leu Glu Gln Tyr Gly Thr Asn Glu Tyr Ser Ile Ile
                325                 330                 335
Ser Ser Met Lys Lys His Ser Leu Ser Ile Gly Ser Gly Trp Ser Val
                340                 345                 350
Ser Leu Lys Gly Asn Asn Leu Ile Trp Thr Leu Lys Asp Ser Ala Gly
            355                 360                 365
Glu Val Arg Gln Ile Thr Phe Arg Asp Leu Pro Asp Lys Phe Asn Ala
370                 375                 380
Tyr Leu Ala Asn Lys Trp Val Phe Ile Thr Ile Thr Asn Asp Arg Leu
385                 390                 395                 400
Ser Ser Ala Asn Leu Tyr Ile Asn Gly Val Leu Met Gly Ser Ala Glu
                405                 410                 415
Ile Thr Gly Leu Gly Ala Ile Arg Glu Asp Asn Asn Ile Thr Leu Lys
                420                 425                 430
Leu Asp Arg Cys Asn Asn Asn Asn Gln Tyr Val Ser Ile Asp Lys Phe
            435                 440                 445
Arg Ile Phe Cys Lys Ala Leu Asn Pro Lys Glu Ile Glu Lys Leu Tyr
450                 455                 460
Thr Ser Tyr Leu Ser Ile Thr Phe Leu Arg Asp Phe Trp Gly Asn Pro
465                 470                 475                 480
Leu

<210> SEQ ID NO 25
<211> LENGTH: 39
<212> TYPE: DNA
<213> ORGANISM: Homo sapiens

<400> SEQUENCE: 25
atatctacaa gcttgcgacc atggaacaac ggggacaga                    39

<210> SEQ ID NO 26
<211> LENGTH: 34
<212> TYPE: DNA
<213> ORGANISM: Homo sapiens

<400> SEQUENCE: 26
ctagatggat cctcagcctc cacctgagca gatg                         34
```

```
<210> SEQ ID NO 27
<211> LENGTH: 39
<212> TYPE: DNA
<213> ORGANISM: Homo sapiens

<400> SEQUENCE: 27
atatctacaa gcttgcgacc atggaacaac ggggacaga                              39

<210> SEQ ID NO 28
<211> LENGTH: 33
<212> TYPE: DNA
<213> ORGANISM: Homo sapiens

<400> SEQUENCE: 28
ctagatggat ccttaggaca tggcagagtc tgc                                    33

<210> SEQ ID NO 29
<211> LENGTH: 34
<212> TYPE: DNA
<213> ORGANISM: Homo sapiens

<400> SEQUENCE: 29
ctagatggat cctcagcctc cacctgagca gatg                                   34

<210> SEQ ID NO 30
<211> LENGTH: 36
<212> TYPE: DNA
<213> ORGANISM: Homo sapiens

<400> SEQUENCE: 30
ccaacaatca aggtttttgc ctccacctga gcagat                                 36

<210> SEQ ID NO 31
<211> LENGTH: 26
<212> TYPE: DNA
<213> ORGANISM: Homo sapiens

<400> SEQUENCE: 31
gtggaggcaa aaaccttgat tgttgg                                            26

<210> SEQ ID NO 32
<211> LENGTH: 34
<212> TYPE: DNA
<213> ORGANISM: Homo sapiens

<400> SEQUENCE: 32
ctagatggat cctcacagcg ggttacccca gaag                                   34
```

VACCINE TARGETING CELLULAR DEATH RECEPTOR DR5

This application claims the benefit of priority to U.S. Provisional Patent Application Ser. No. 61/111,798, which was filed on Nov. 6, 2008, and which is incorporated herein by reference.

GRANT INFORMATION

Research in this application was supported in part by a grant from the Department of Defense DOD W81XWH-07-1-0521, National Institute of Health (NIH Grant No. NIH CA 76340). The Government has certain rights in the invention.

TECHNICAL FIELD

The invention relates to the field of vaccines which induce a host to produce antibodies against self antigens and particularly antigens that agonize death receptors of cells within the body of a host; the vaccines induce apoptosis in target cells and are useful in the treatment of cancer and other chronic diseases in which the apoptosis of target cells is desired.

BACKGROUND OF THE INVENTION

There is a pressing need for new regimens to treat existing cancers and prevent their recurrence. A recently developed strategy that shows great promise is the induction of tumor cell apoptosis (programmed cell death) through the triggering of death receptors expressed on tumor cell surfaces.

Cell apoptosis (programmed cell death) is a normal process through which cells of the body are induced to commit suicide when they are aged, damaged, or under attack by the immune system. For example, one mechanism for the elimination of virally infected, foreign, and tumor cells is the induction of apoptosis in these cells by attacking cytolytic T cells and other immune effector cells (Smyth et al., 2003; Bolitho et al., 2007). Apoptosis may have evolved as a mechanism to produce cell death without harming the host through such phenomena as the release of toxic oxidants and DNA that occurs in necrosis. In apoptosis, cells are disassembled in an orderly way, with the debris packaged in vesicles for uptake by scavenger cells, including antigen presenting cells (Ramachandran et al., 2000).

Apoptosis can be induced through two signaling pathways: the intrinsic pathway, which is activated by intracellular mitochondrial signals, or the extrinsic pathway, which is initiated through engagement of pro-apoptotic surface receptors (Duiker et al., 2006; Ashkenazi et al., 2008). The intrinsic pathway mediates apoptosis in response to intracellular changes such as DNA damage. This is the mode of cell death triggered by aging and by chemo- or radiotherapy induced damage. The extrinsic pathway is triggered by the activation of death receptors of the tumor necrosis factor receptor (TNFR) superfamily. Agonists of these death receptors induce them to transduce death signals into the cell interior. The superfamily includes families of receptors for TRAIL, Fas ligand, and TNF-alpha.

The TRAIL family of receptors contains the most promising targets for cancer therapy or prophylaxis. They are so named because they induce apoptosis when agonized by tumor necrosis factor-related apoptosis inducing ligand (TRAIL). Of the five known TRAIL receptors, DR4 (TRAIL-R1) and DR5 (TRAIL-R2) are therapeutic targets, because agonists of these receptors trigger cell death (Hampton, 2006; Cretney et al., 2007; Rowinsky 2005; Shi et al; 2005; Clancy et al., 2005). The other three TRAIL receptor family members are decoy receptors, which do not transmit death signals (DcR1; DcR2; OPG). The genes encoding DR4 and DR5 are highly homologous and likely arose from a common ancestral gene (Guan et al., 2001). In mice, only one agonist TRAIL receptor, DR5, has been identified. It is highly homologous in both structure and function to both human DR5 and human DR4 (Wu et al., 1999). DR4 and/or DR5 are expressed in both solid tumors and hematological malignancies and in some normal tissues such as hepatocytes, myocytes, glial tissue, bronchial and alveolar epithelium and activated lymphocytes.

Tumor cells tend to be far more susceptible than their normal counterparts to apoptosis induced by TRAIL receptor ligation. The mechanism that allows TRAIL to preferentially induce apoptosis in tumor cells, while sparing most normal cells, is not fully understood, but may be associated with the expression of common oncogenes, such as myc and ras that sensitize cancer cells to the extrinsic pathway of apoptosis (Ashkenazi et al., 2008). In addition, relative levels of TRAIL death receptors, decoy receptors and apoptosis inhibitors such as FLIP, IAP or XIAP also impact susceptibility (Duiker et al., 2006). Other death receptor families such as Fas are less tumor specific in occurrence and action, but may also be potential targets for therapy.

One strategy for exploiting TRAIL death receptors for therapeutic purposes is to administer recombinant TRAIL to a tumor host. Another is to administer antibodies to the TRAIL receptor, which bind to and agonize that receptor, essentially mimicking TRAIL. Ongoing and completed Phase I and II clinical trials using these reagents are showing clinically promising outcomes with little clinical toxicity and several instances of disease stabilization. Mapatumumab a DR4 agonist mAb, was administered at doses up to 20 mg/kg in a phase I trial (Hotte et al., 2008). The treatment was well tolerated and maximum tolerated dose was not reached. Of 41 patients with solid tumor, 12 showed stable disease with median duration of 3.5 months. Lexatumumab (HGS-ETR2), a DR5 agonist mAb, was tested in 37 patients and 10 mg/kg was the maximum tolerated dose when administered every 21 days up to 43 cycles (Hotte et al., 2008). Twelve patients had durable stable disease that lasted for ~4.5 months. Further testing of both mAb is on-going in open trials.

Unfortunately, monoclonal antibody regimes, essentially "passive immunotherapy", are impractical for the prolonged treatments required for chronic diseases like cancer. There are two main problems. First, clinical monoclonal antibodies are extremely expensive to manufacture. They are produced through recombinant or hybridoma technology, and must be purified to meet clinical safety standards. Once administered, they have a serum half life on the order of 11-18 days and typically must be administered at two week intervals (Tolcher et al., 2007). Second, exogenous antibodies have the possibility of provoking host immune responses to themselves. Effects of this response can range from rapid neutralization of the antibody to the induction of inflammatory disease (Abhinandan et al., 2007). Once an immune response against a monoclonal antibody is established, it permanently renders the antibody useless for therapy.

The problems of great expense and anti-antibody response limit or destroy the usefulness of recombinant TRAIL and exogenous anti-TRAIL receptor antibodies in cancer treatment. Therapeutic treatment cannot be maintained for the prolonged periods needed to eliminate existing tumor, and to render lifelong protection. Lifelong prophylaxis may be necessary to prevent the development of metastases after elimination of primary tumor, and also to prevent primary tumors in individuals at high genetic or environmental risk of cancer.

These drawbacks of treatment with exogenous TRAIL and anti-TRAIL receptor antibodies are avoided when anti-TRAIL death receptor antibodies are induced in the host by a vaccine against TRAIL receptors. The host's own immune system will continue to produce antibodies for many years, with no risk of an immune response against any portion of the antibody. The only cost is that of a course of vaccination. Limited serum half life is not a problem when the antibody is produced continuously. Indeed, antibody production may be enhanced when TRAIL death receptor-expressing tumor cells reappear, thanks to the specific memory property of B cell responses.

The main roadblock to the development of a therapeutic or prophylactic vaccine against host cell death receptors has been the phenomenon of tolerance, the immune system's safeguard against autoimmune disease. Death receptors are self antigens. The immune system generally becomes tolerant to self antigens early in life. T lymphocyte clones specifically reactive to self antigens are either deleted or anergized during thymic development, or are kept in check at the periphery, mainly by diverse populations of regulatory T cells (Treg). Especially important are natural Treg which develop in the thymus upon high affinity recognition of antigens in the thymic stroma (Colombo and Piconese, 2007). It is often impossible to define an antigen and immunization protocol that will break tolerance to a self antigen to achieve effective vaccination. This problem has defeated the development of many vaccines intended to induce immune response against tumor antigens (Wei et al, 2004). This is equally true of vaccines intended to induce antibodies, as helper T cell aid is essential for most B cell responses.

Another roadblock to the development of an agonist anti-death receptor vaccine is the need for a fully competent immune system that can meet the challenge of mounting a response to a self antigen. Cancer patients are often immunocompromised by their disease. Regulatory T cells play a role here too, as do tumor-induced myeloid suppressor cells and immunosuppressive factors secreted by tumors (Widen et al., 2008). Chemotherapy and radiation treatments also suppress response. Because of immunosuppression, many cancer patients cannot respond to self antigens, including many of the self antigens overexpressed or inappropriately expressed on tumor cells (Wei et al., 2004). Finally, the long lived antibody titers induced by effective vaccinations may bring out side effects of death receptor agonism which are not apparent in short term treatments.

SUMMARY OF THE INVENTION

The present invention provides a therapeutic for vaccinating a mammalian host to produce agonist antibodies which trigger specific death receptors borne by its own cells, to induce long term protection against target cells expressing the specific receptors, with minimal side effects. Accordingly, the invention provides means and methods for immunizing a mammalian host against a cellular death receptor, and for overcoming immunological tolerance to that receptor where necessary. The target cells include cells selected from the group of solid tumors such as colorectal, ovarian, breast, prostate, non-small cell lung, pancreatic, head and neck, and skin cancers, as well as hematopoietic tumors such as lymphomas, leukemias, and multiple myeloma.

The compositions provided by the invention are vaccines that induce agonist antibodies against mammalian cellular death receptors, including those of human origin. One object of the invention is to immunize against death receptors of the TNF receptor superfamily and more particularly the TRAIL receptors DR4 and DR5. The vaccine may be a genetic vaccine comprising a polynucleotide, which causes one or more death receptor peptides to be expressed in a host and to be presented as an antigen to induce a specific immune response. The polynucleotide of one vaccine encodes antigenic peptides derived from the extracellular domain of DR5, or alternatively from the transmembrane domain, or alternatively from both. In one form of the vaccine, a peptide of the extracellular domain of murine DR5 is encoded by the polynucleotide of SEQ ID NO: 1 (deduced amino acid sequence SEQ ID NO: 2), or by sequences having at least 70% identity to SEQ ID NO: 1; and the transmembrane domain of murine DR5 is encoded by a vaccine polynucleotide of SEQ ID NO: 3 (deduced amino acid sequence SEQ ID NO: 4), or by sequences having at least 70% identity to SEQ ID NO: 3. In another form of the invention, a peptide of the extracellular domain of human DR5 is encoded by a vaccine polynucleotide of SEQ ID NO:5 (deduced amino acid sequence SEQ ID NO: 6), or by sequences having at least 70% identity to SEQ ID NO: 5; and the transmembrane domain of human DR5 is encoded by a vaccine polynucleotide of SEQ ID NO: 7 (deduced amino acid sequence SEQ ID NO:8), or by sequences having at least 70% identity to SEQ ID NO: 7.

The invention provides additional compositions to further increase the immunogenicity of the vaccine and thus its ability to break tolerance. In one form of the invention, this increased immunogenicity is provided by the expression of a polynucleotide encoding a peptide, which is a fusion product of a death receptor antigen and an adjuvant peptide. In one alternative, this fusion peptide encodes the extracellular domain of DR5 and tetanus toxin fragment td1, an immunogenic but nontoxic peptide of tetanus toxin fragment C domain 1, or alternatively tetanus toxin fragment p30. In another form of the vaccine, immunogenicity is increased by fusing the polynucleotide sequence encoding a self death receptor antigen with a segment of a xenogenic death receptor antigen. For example, a human may be immunized with an extracellular DR5 domain that is a hybrid human-rat polypeptide of SEQ ID NO: 9 (deduced amino acid sequence SEQ ID NO: 10) or a sequence having at least 70% homology to SEQ. ID NO: 9.

The invention has broad application provided by a variety of vectors and vehicles for the delivery of the genetic vaccines for maximum immunogenic effect. In a preferred embodiment, the vaccine is delivered as a naked DNA plasmid. Alternative vectors include a retrovirus vector, an adenovirus vector, a vaccinia virus vector, a poxvirus vector, an adeno-associated virus vector, a lentivirus vector, a virus like particle, a *Salmonella* vector, a *Shigella* vector, a *Listeria* vector, a *Yersinia* vector, and an *Escherichia* vector.

The invention also provides methods for employing the vaccine in a mammalian subject, including a human. The methods include administering an effective amount of a vaccine that induces agonist antibodies to a death receptor, and inducing apoptosis in target cells through the agonistic action of those agonist antibodies. Other immune responses such as antibody dependent cell mediated cytotoxicity may also contribute to target cell killing.

The invention also provides methods for employing the vaccine in a prophylactic setting. The vaccine may be administered to prevent the initiation of target cell populations in the body, for example populations of tumor cells newly arising in an individual at high risk of cancer, or nests of tumor cells metastasizing from a primary tumor. The vaccine may alternatively be administered in a therapeutic setting, to reduce or eliminate existing target cell populations in the body, for example the cells of tumors existing at the start of treatment.

Methods are also provided for treatments that work in combination with the vaccine to further increase immunogenicity or tolerance breaking power. In one form of the invention, the vaccine is combined with or accompanied by cytokines, which encourage the maturation and antigen presentation capabilities of dendritic cells and other antigen presenting cells and thereby further increase tolerance breaking effect. For example, GM-CSF is administered in soluble form or as a nucleic acid vector, which results in GM-CSF expression at a vaccination site. In another form of the invention, the host is transiently depleted of tolerance promoting regulatory T cells through the administration of antibodies to surface markers of those T cells. In one method, the antibody is anti-CD25.

In order to respond to vaccines against self antigens, a host must possess an immune system sufficiently competent to overcome tolerance in response to vaccination. This is true not only for vaccines against death receptors but also for those against most tumor antigens. The invention provides a method for determining whether a host is capable of making such a response. An effective amount of vaccine known to induce antibodies to a death receptor in an immunocompetent host is administered to a mammalian subject, including a human patient. Immunocompetent subjects are those that produce detectable amounts of antibodies to that death receptor.

BRIEF DESCRIPTION OF THE DRAWINGS

Other advantages of the present invention are readily appreciated as the same becomes better understood by reference to the following detailed description when considered in connection with the accompanying drawings wherein:

FIG. 1. shows a diagram of two gene constructs, each encoding a death receptor polypeptide which is a hybrid of mouse and rat DR5 sequences, and of tetanus toxin fragment td1, Mouse, rat, and tetanus toxin sequences are symbolized as in legend; SP=signal peptide;

FIG. 2A shows schematic diagrams of two genetic vaccine plasmids against murine DR5; lower plasmid provides fluorescence detection of antigen expression. pV=pVAX1 vector.

FIG. 2B shows schematic diagrams of three genetic vaccine plasmids against human DR5, Abbreviations are as described in the legend;

FIG. 3 shows a diagram of the expression vector plasmid pVAX1™;

FIG. 4 shows a diagram of expression vector plasmid pVAX/mDR5ectm-td1 that renders expression of the extracellular and transmembrane domains of murine DR5 fused to the peptide of tetanus toxin fragment C domain 1 (td1);

FIG. 5 shows a diagram of expression vector plasmid pVAX/mDR5ectm-IRES-eGFP, which encodes peptides of murine DR5 extracellular and transmembrane domains, followed by an IRES element that renders co-expression of the fluorescent protein eGFP;

FIG. 6 shows a diagram of expression vector pVAX/hDR5, which renders expression of wild type human DR5;

FIG. 7. shows a diagram of expression vector pVAX/hDR5ectm, to render expression of peptides of the extracellular and transmembrane domains of human DR5;

FIG. 8. shows a diagram of expression vector pVAX/hDR5ectm-td1, which renders expression of peptides of the extracellular and transmembrane domains of human DR5 fused with tetanus toxin fragment C domain 1 (td1);

FIG. 9A shows flow cytometric histograms representing levels of expression of DR5 on a variety of murine tumor cell lines including BALB/c mouse mammary tumor lines TUBO, D2F2, 4T1, and C57BL/6 lung epithelial tumor line TC-1. Filled histograms represent staining with MD5-1, mAb to mouse DR5 (filled histograms); unfilled histograms represent staining with isotype control;

FIG. 9B. shows a diagram of pVAX/mDR5ectm-td1, a plasmid for the expression of murine DR5 extracellular and transmembrane domains fused with td1;

FIG. 9C. shows a diagram of pVAX/mDR5ectm-IRES-eGFP, a vector which renders the expression of murine DR5 extracellular and transmembrane domains co-expressed with green fluorescent protein eGFP;

FIG. 9D shows a set of flow cytometric dot plots showing the increase in humoral response of mice to a progressive series of vaccinations with pVAX/mDR5ectm-td1 and pGM-CSF. mDR5 antibodies in immune sera were measured by binding of anti-mouse-Ig (red fluorescence, abscissa) to antibodies that bound D2F2 cells which had been transiently transfected with pVAX/mDR5ectm-IRES-eGFP (green fluorescence, ordinate). Cells expressing DR5 and binding anti-DR5 antibodies are represented in the upper right quadrant. The percentage of total cells represented by these dual-stained cells is also listed in the upper right quadrant. The left hand panel shows positive control staining with a purified mouse anti DR5 monoclonal antibody, MD5-1 (aDR5);

FIG. 9E shows histograms of flow cytometric analysis of staining of the human ovarian cancer cell line SKOV3 with monoclonal antibody to murine DR5, MD5-1. In the left panel, SKOV3 cells transfected with control vector display no staining over isotype control (empty peak vs. filled peak). In the right panel, SKOV3 transfected with murine DR5 displays staining of nearly 100% of cells. pV, pVAX1 DNA vaccine vector purchased from Invitrogen (Cat#26020); SP, DR5 signal sequence; ecd, extracelluar domain (of DR5); tm, transmembrane domain (of DR5); td1 Tetanus toxin fragment C domain 1; IRES, Independent Ribosome Entry Site;

FIG. 10 shows a plot of tumor incidence in mice vaccinated against TRAIL receptor family member DR5 and challenged with mammary tumor D2F2;

FIG. 11A shows staining of MDA-MB231 human breast cancer cells with serum from mice immunized with genetic vaccine pVAX/hDR5 (hDR5 immune sera), compared to staining with a known anti-DR5 antibody (hDR5 mAb);

FIG. 11B shows a flow cytometric analysis of apoptosis, with Annexin-V staining represented as green fluorescence on the abscissa and 7-AAD staining represented as red fluorescence on the ordinate; and FIG. 11C compares the morphology of cells treated with immune and preimmune sera, as well as positive controls known to induce apoptosis.

FIG. 12A shows a scheme for electrovaccinating mice with pVAX-hDR5, encoding full length wild type human DR5;

FIG. 12B shows flow histograms comparing the specific binding of a known anti-human DR5 antibody to hDR5 transfected NIH3T3 cells (top panel, filled histogram) versus the specific binding of serum antibodies of anti-hDR5-immunized mice to the same cell line (bottom panel, filled histogram); open histograms represent binding of nonimmune control serum antibodies;

FIG. 12C shows a plot representing the levels of anti-hDR5 antibodies induced by immunization, as determined by ELISA using chimeric hDR5 (aa 1-182);

FIG. 12D shows flow histograms comparing the specific binding of a known anti-human DR5 antibody to the human TNBC cell line SUM159 (top panel, filled histogram) versus the specific binding of serum antibodies of anti-hDR5-immunized mice to the same cell line (bottom panel, filled histogram); open histograms represent binding of nonimmune control serum antibodies;

Figure 13:
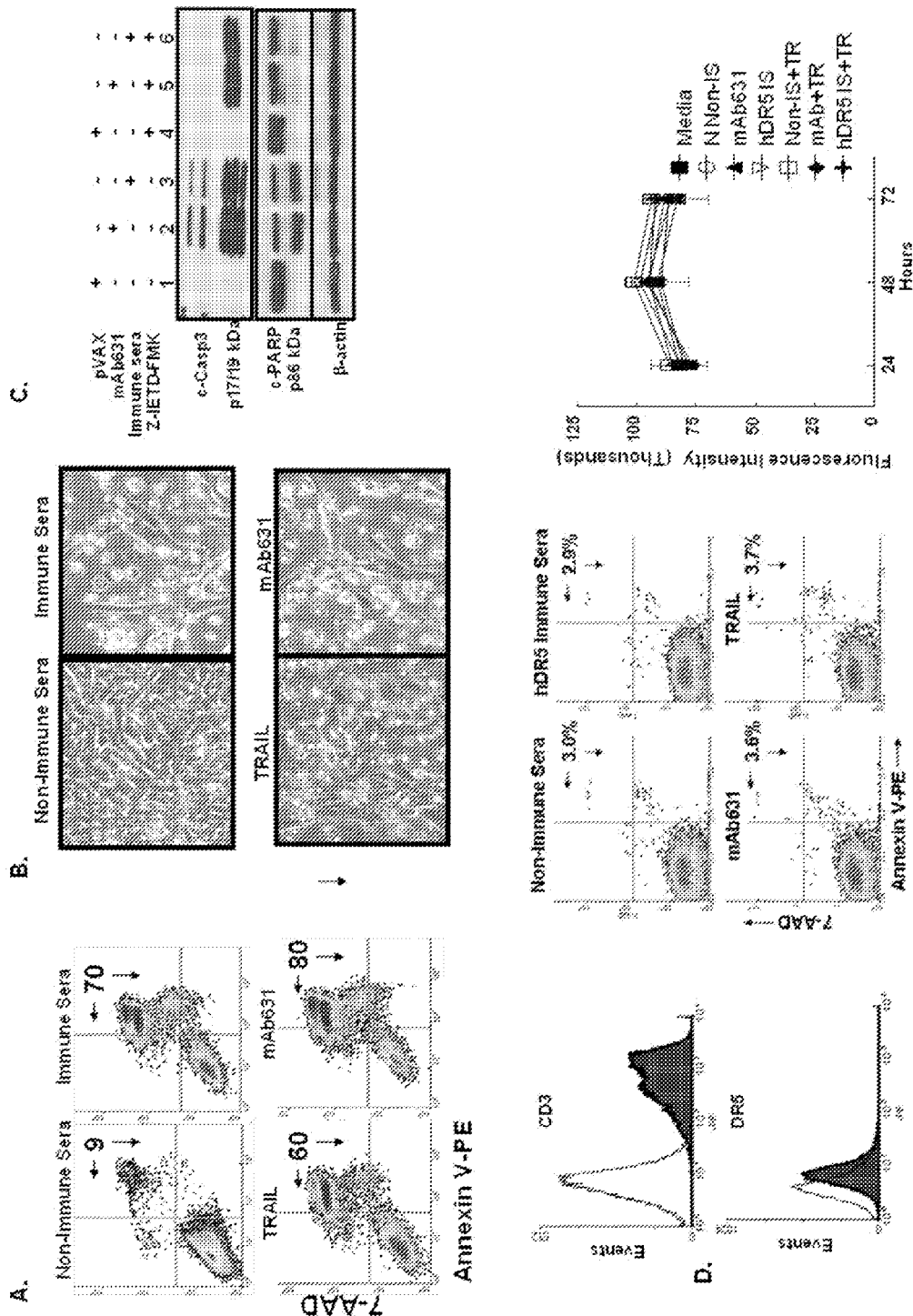
FIG. 13A shows a two color fluorescence plots of the results of Annexin V+7AAD apoptosis assays wherein SUM159 cells were treated 20 h with serum from mice vaccinated with pVAXhDR5 (immune sera) or with pVAX control (Non-Immune Sera); or treated with hDR5 agonists, mAb631 (5 μg/mL) or TRAIL (1 μg/m L)

FIG. 13B shows representative photomicrographs of cultures of cells represented in the Annexin V+7AAD assay shown in FIG. 13A. B. Cell cultures were harvested and analyzed for apoptosis using Annexin V and 7+AAD. Percentages represent total apoptotic cells;

FIG. 13C shows Western blot analysis of whole cell lysates of SUM159 which had been treated for 5 hours with 2% non-immune (pVAX) or immune (pVAXhDR5) sera or 5 □g/mL mAb631 in the absence or presence of Caspase-8 inhibitor, Z-IETD-FMK; the top panel shows analysis of cleavage products of Caspase 3, the middle panel shows analysis of cleavage products of PARP, and the bottom panel shows β-actin used to normalize the results; and FIG. 13D shows flow histograms (left panel) demonstrating the expression of CD3 and DR5 (filled histograms) by activated human peripheral blood T cells, with open histograms representing of negative controls; two color fluorescence plots (middle panel) of the results of Annexin V+7AAD apoptosis assays wherein activated human T cells were treated with serum from mice vaccinated with pVAXhDR5 (Hdr5 immune sera) or with pVAX control (Non-Immune Sera); or treated with hDR5 agonists, mAb631 or TRAIL, and a plot of the results of an Alamar Blue® viability assay of activated human T cells during treatment with various DR5 agonists and controls (right panel); "non-IS"=non immune serum; "TR"=TRAIL. were activated from peripheral blood to demonstrate upregulation of cell surface DR5 expression and resistance to DR5 agonist induced apoptosis and growth inhibition.

Figure 14:
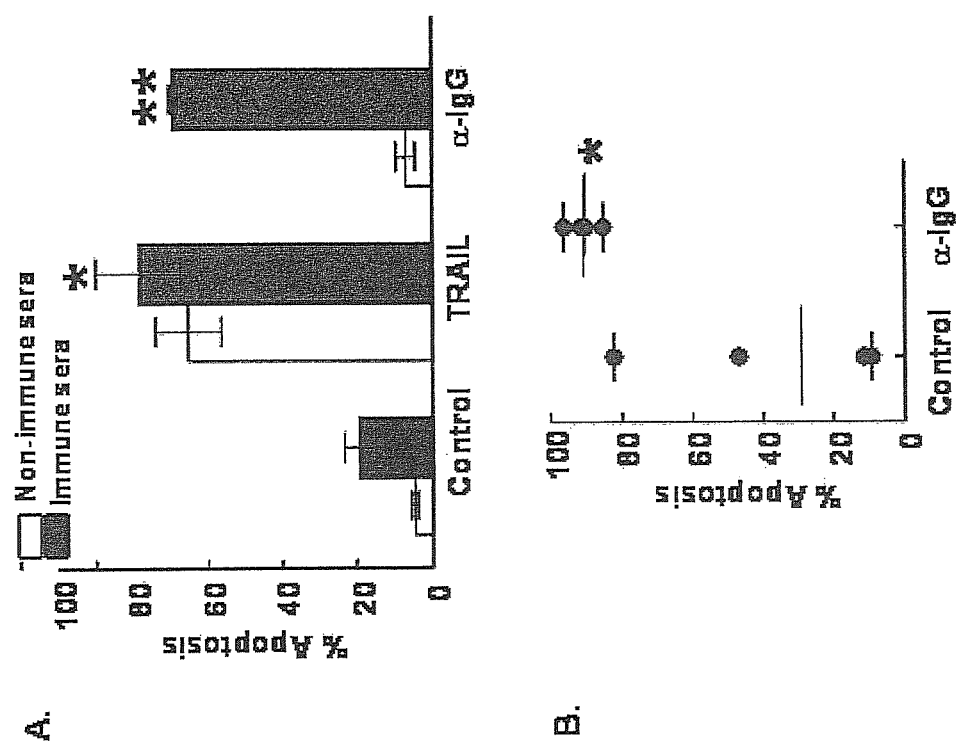

FIG. 14A shows a plot representing the apoptotic effects of anti-hDR5 antibodies induced by anti-hDR5 vaccine, and the amplification of these effects by treatment with TRAIL or by cross-linking with anti-mouse IgG (α-IgG), as determined by Annexin V+7AAD staining; SUM159 cells were treated with either 1% immune or nonimmune sera for 30 minutes, washed, and treated 20 hours with either nonimmune goat IgG at 10 μg/ml (Control), TRAIL at 1 μg/ml, (TRAIL) or goat anti-mouse IgG at 10 μg/ml (α-IgG); *p<0.2, **p<0.005; and FIG. 14B shows a plot representing the apoptotic effects of 4 different batches of sera of individual mice vaccinated with pVAX-hDR5 upon SUM159 cells and its amplification by cross linking by goat anti-mouse IgG; *p<0.22.

Figure 15:
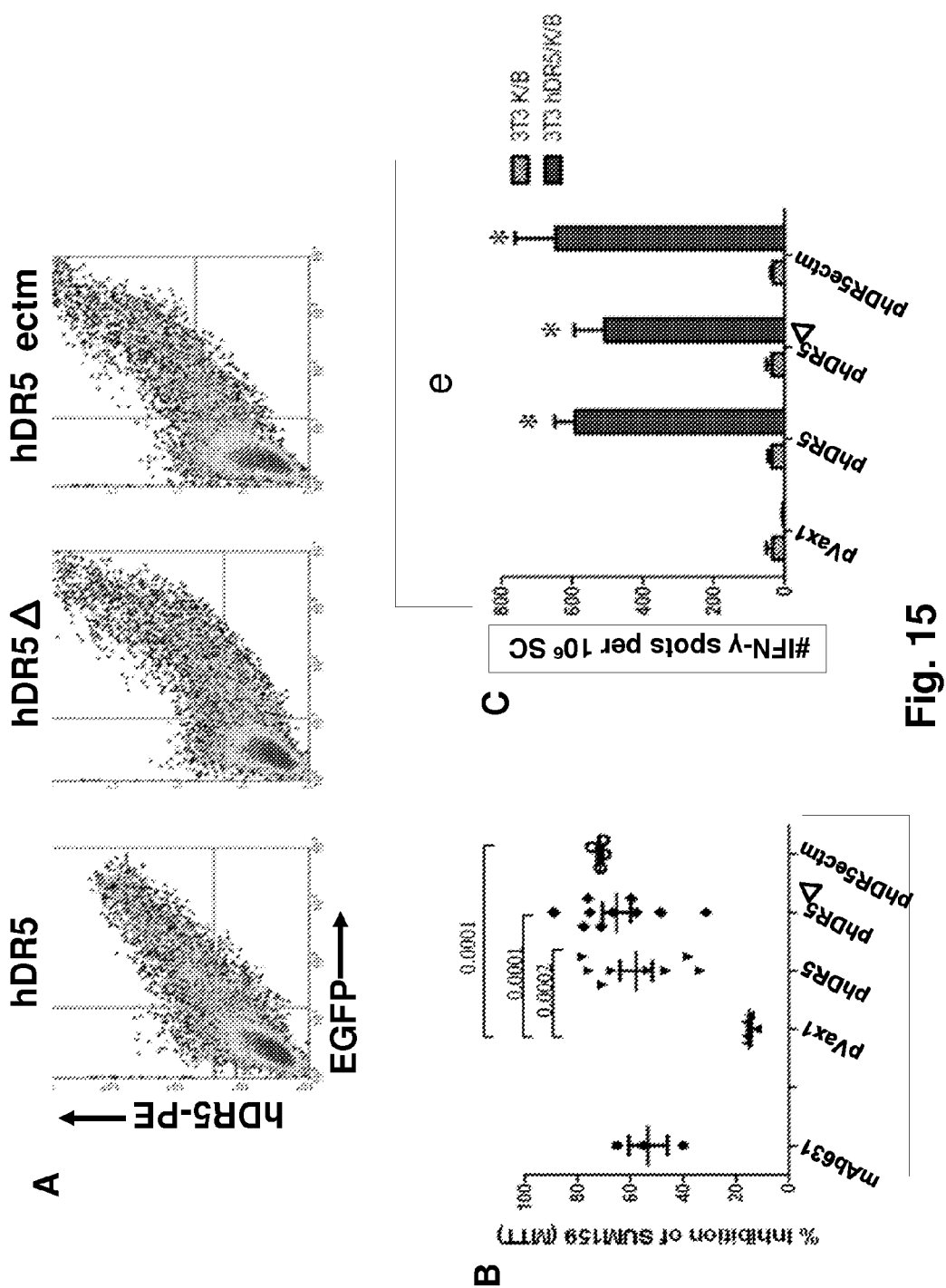

FIG. 15A shows a flow cytometric analysis of the cell surface expression of hDR5 after co-transfection of NIH3T3 cells with EGFP and a vaccine construct encoding either wild type hDR5 (hDR5), hDR5 with truncated intracellular death domain (hDR5▲), or the extracellular and transmembrane domains of hDR5 (hDR5 ectm); cell surface expression of hDR5 is indicated by staining with mAb HS201 and a PE-conjugated secondary antibody (y Axis);

FIG. 15B shows a plot representing the growth inhibitory effects of immune sera induced by vaccination with three different hDR5 constructs, compared to the effects of control sera obtained after vaccination with control vector (pVAX1) and also compared to the effects of a known hDR5 agonist antibody (mAb631). pVAX1=control vector; phDR5=pVAX1 vector encoding full length wild type hDR5; phDR5▲=pVAX1 vector encoding hDR5 with truncated intracellular death domain; pVAX-hDR5ectm=pVAX1 vector encoding extracellular domain and transmembrane regions of hDR5, but without DR5 intracellular sequences; and FIG. 15C shows a plot representing the frequency of γ-interferon producing T cells in spleen cell populations harvested from vaccinated mice and exposed to antigen presenting cells (APC) engineered to express human DR5, MHC Kd and B7.1 (3T3 hDR5/K/B), or to control APC expressing only MHC Kd and B7.1 (3T3 K/B). pVAX1=control vector; phDR5=pVAX1 vector encoding full length wild type hDR5; phDR5▲=pVAX1 vector encoding hDR5 with truncated intracellular death domain; pVAX-hDR5ectm=pVAX1 vector encoding extracellular domain and transmembrane regions of hDR5, but without DR5 intracellular sequences.

FIG. 16A show a plot representing the rate of occurrence of palpable tumors of human SUM159 breast cancer cells in SCID mice, after mice were injected with cells precoated with immune sera induced by vaccination with pVAXhDR5 (hDR5 immune sera), or with control sera obtained after vaccination with control vector (pVAX control), or with hDR5 agonist antibody (mAb631); and FIG. 16B shows a plot representing the rate of growth of tumors of human SUM159 breast cancer cells in SCID mice, after mice were injected with cells precoated with immune sera induced by vaccination with pVAXhDR5 (hDR5 immune sera), or with control sera obtained after vaccination with control vector (pVAX control), or with hDR5 agonist antibody (mAb631).

DETAILED DESCRIPTION OF THE INVENTION

The invention provides a novel and innovative approach to therapies based on the exploitation of the death receptors of tumor cells and other target cells. It provides a means for inducing a mammalian host to produce antibodies that agonize death receptors of target cells. Essentially, the invention is a vaccine which causes the host to engage in the long term manufacture of its own native and well tolerated version of existing commercial antibodies, such as anti-TRAIL receptor antibodies, which, though clinically promising, are not feasible for long term treatment. Furthermore, because of the specific memory property of the B cell response, the manufacture of agonist antibodies is stepped up when tumor cells bearing the target death receptor reappear at primary or metastatic sites long after successful initial treatment. Finally, because the antibodies produced by the host are polyclonal, and are produced by a living immune system that adapts to antigen variants via epitope spreading, tumors are less likely to become resistant to host-manufactured antibodies than they are to commercial anti-TRAIL receptor antibodies, which are monoclonal.

A key factor in the utility of the invention is a set of antigens sufficiently immunogenic to defeat the tolerance to self proteins that makes immunization against one's own TRAIL receptors so difficult to achieve. Where still greater immunogenicity is desired, the invention also provides the antigens as polypeptides fused to "helper" adjuvant peptides, along with methods for reducing the tolerogenic effects of regulatory T cells, and for enhancing antigen presentation.

One embodiment of the invention is a vaccine against the TRAIL receptor DR5 which occurs in many mammalian species including humans. Other receptors, which may be similarly targeted, include the very similar DR4, another inducer of apoptosis, and any other cell surface receptors that induce apoptosis upon binding to a ligand-mimicking antibody. These antibodies trigger apoptosis of target cells by triggering death receptors to initiate an extrinsic signal transduction pathway leading to apoptosis.

In the case of DR5, binding of the natural ligand TRAIL induces DR5 to trimerize in cell membranes, leading to precise positioning of DR5 transmembrane helices and cytosolic domains, followed by the formation of a death-inducing signaling complex (DISC). Through the adaptor protein FADD in the DISC, initiator caspase 8 is recruited and activated to trigger the activation of downstream effector caspases 3, 6 and 7. Recent evidence indicates that agonist antibodies to DR5 also constrain the receptors to trimerize and initiate apoptotic signaling (Wassenaar et al., 2008)

Elements of the intrinsic pathway of apoptosis can also be recruited. In addition, the binding of antibody to death receptor may promote apoptosis through antibody dependent cellular cytotoxicity (ADCC). In this indirect mode of immune attack, killer cells armed with Fc receptors, bind antibody-coated target cells to cause death. These killers include macrophages and NK cells, and natural killer cells.

In one embodiment of the invention, the antigen is delivered as a component of a genetic vaccine containing a DNA encoding at least one peptide of a death receptor. The DNA also includes essential regulatory elements such that the DNA is transcribed and translated into peptides upon introduction into a living cell. The peptides are then processed by antigen presenting cells to induce immune response. The invention is not limited to DNA and may alternatively comprise at least one RNA molecule.

In a preferred embodiment, the antigen is provided by DNA encoding the extracellular and transmembrane domains of mouse DR5 (mDR5ectm) (SEQ ID NO: 11; deduced amino acid sequence SEQ ID NO: 12). In another preferred embodiment, the antigen is provided by DNA encoding the extracellular and transmembrane of human DR5 (hDR5ectm) (SEQ ID NO: 13; deduced amino acid sequence SEQ. ID. NO: 14). Any smaller but still immunogenic fragments of the above mentioned domains may of course be alternatively used. In all disclosed constructs, mouse DR5 sequences are derived from Accession #NM_020275, all human DR5 sequences are derived from Accession #NM_147187, and all rat sequences are derived from Accession #XM_344431.

Figure 1:
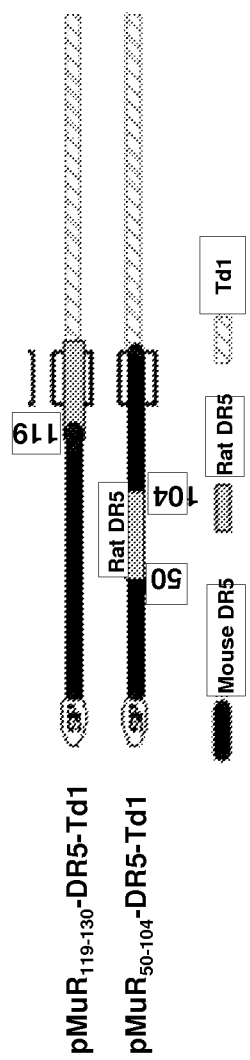

The immunogenicity of the DR5 antigen can be further increased by encoding it as an interspecies hybrid. Examples include $MuR_{119-130}$-DR5 and $MuR_{50-104}$-DR5, each of which encode a stretch of rat DR5 within a larger stretch of murine DR5 (FIG. 1, mouse and rat sequences). See SEQ ID NO: 19 for example polynucleotide sequence and SEQ ID NO: 20 for deduced amino acid sequence. Human rat hybrids can also be constructed. See SEQ ID NO: 9 for polynucleotide and SEQ ID NO: 10 for deduced amino acid sequence. It will be understood by those skilled in the art that hybrid forms can induce increased immune response while preserving the specificity of the immune response to the host's native epitope.

In still another preferred embodiment, immunogenicity of the DR5 antigen can be alternatively or additionally increased by encoding it as a fused combination of the antigen and an adjuvant peptide. For example, a polynucleotide encoding the immunogenic but nontoxic peptide tetanus toxin fragment C domain 1 (td1) was fused to mDR5-ectm to produce the polynucleotide mDR5-td1 (FIG. 2; SEQ ID NO 15; deduced amino acid sequence SEQ ID NO 16). In another example, the adjuvant peptide component is provided as P30, a fragment of td1 containing universal epitopes presented by multiple human MHC (Panina-Bordignon et al., 1989). Those skilled in the art will understand that similar increases in immunogenicity can be provided by other adjuvant peptides, delivered as fusion polypeptides or as free products, including but not limited to heat shock protein 70, cholera toxin subunits, and PADRE (Mocellin et al., 2004).

To aid in detecting and quantitating the expression of the antigen in vitro or in vivo, the polynucleotide encoding the antigen can be linked to a polynucleotide encoding a marker which may be detected by fluorescence or chemical reaction. In preferred embodiments, an antigen-adjuvant polypeptide is coexpressed with a gene encoding the enhanced green fluorescent protein eGFP. For example a bicistronic construct was developed for murine DR5 antigen (Example 1, FIG. 9C and SEQ. ID NO: 17, for deduced amino acid sequences of the two separately expressed peptides, see SEQ ID NO: 18). A bicistronic construct can also be provided for human DR5 antigen (see FIG. 2, bottom figure). Other marking and tracking proteins known in the art can be alternatively employed.

Figure 2:
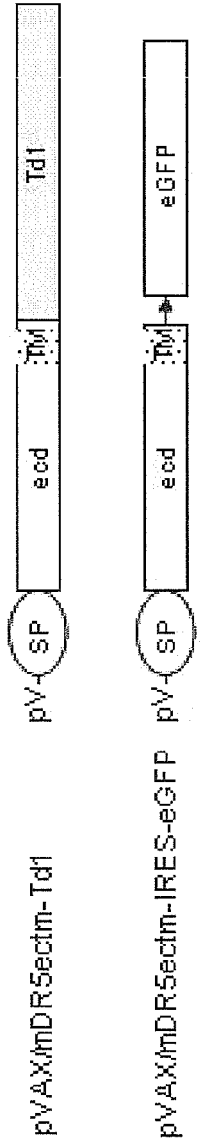
Figure 2:
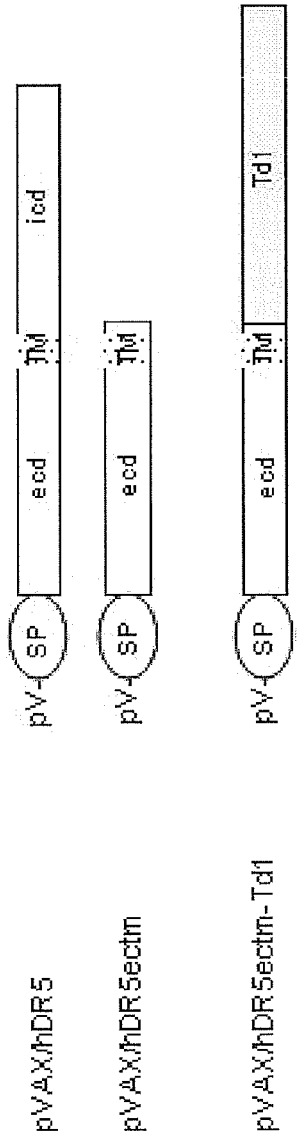
Figure 7:
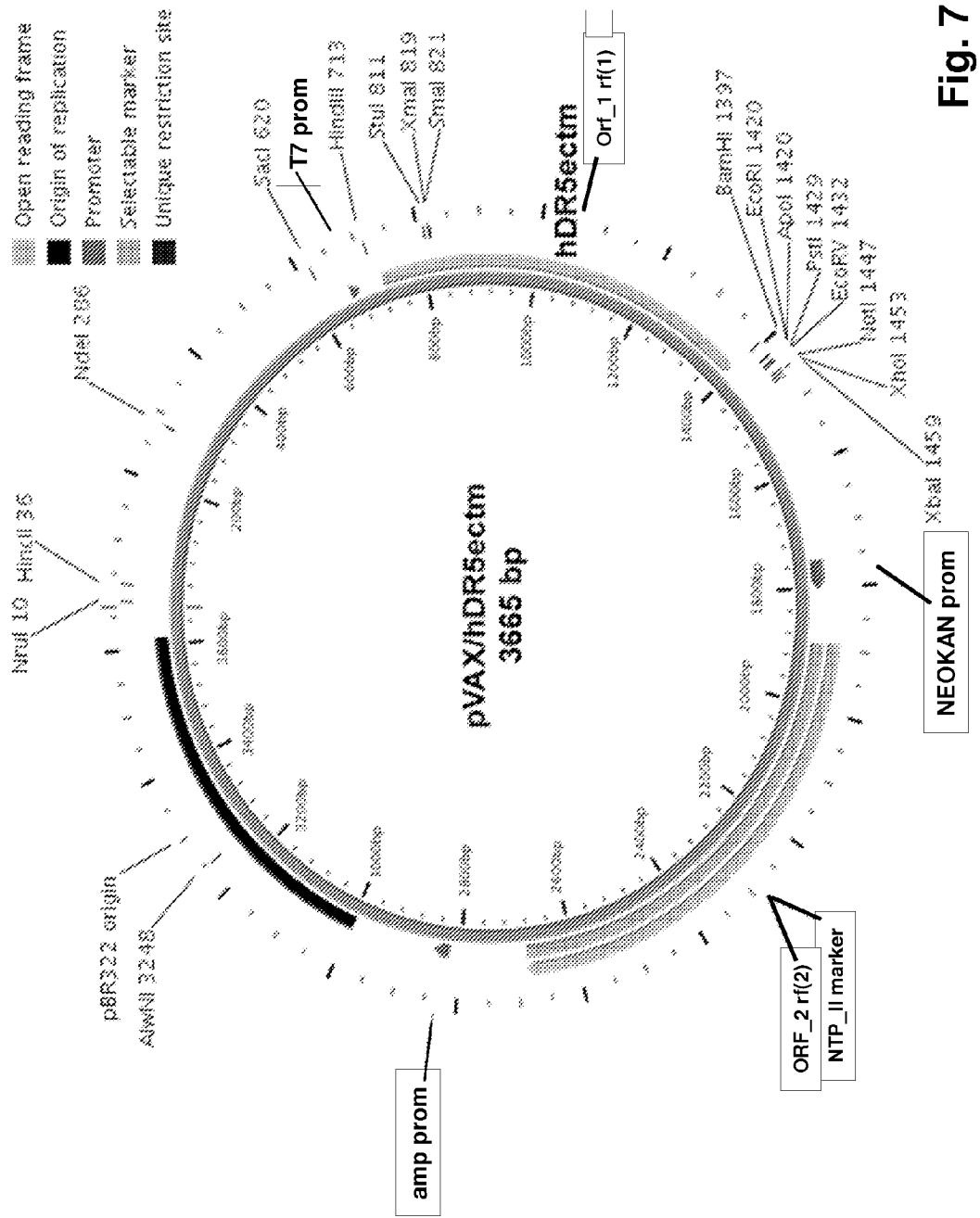
Figure 8:
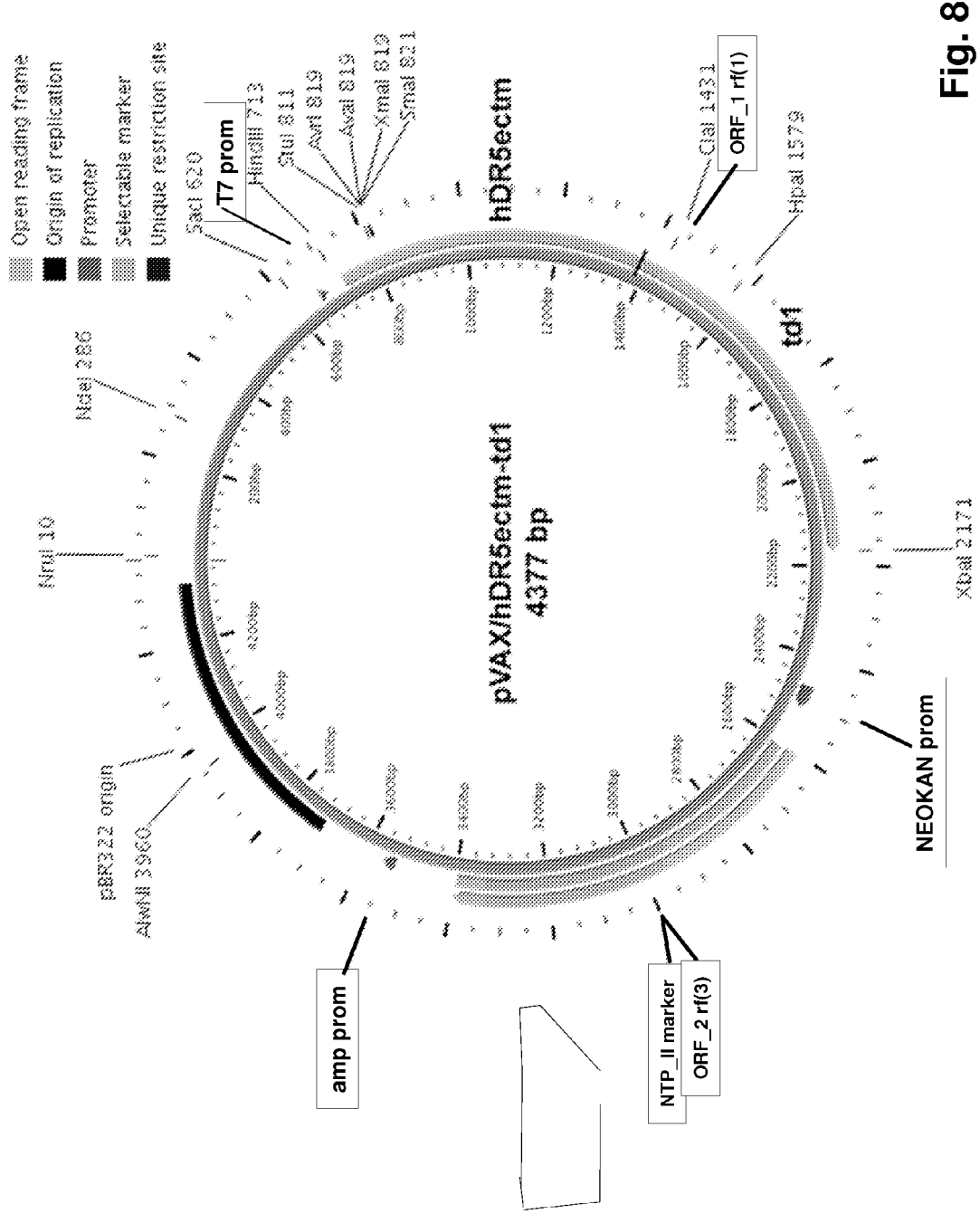

In a preferred embodiment, the polynucleotides of the invention are provided with appropriate linkers and ligated into the expression vector pVAX1™ (Invitrogen™). This vector supplies regulatory sequences necessary for replication in bacteria and for transcription, translation, and expression, in mammalian cells in vitro and in vivo, including the human CMV Immediate Early mammalian transcription promoter, BGH polyadenylation signal region, kanamycin-neomycin (phosphotransferase) resistance gene, and the pBR322 origin of replication (see FIG. 3). pVAX1™ also supplies restriction enzyme sites (Multiple Cloning Site (MCS)), for the insertion of additional genes and selection markers. Vaccine constructs in pVAX1™ were developed for murine DR5, including pVAX/mDR5ectm-td1 and pVAX/mDR5ectm-IRES-eGFP (Example 1, FIG. 2 A, and with vector details in FIGS. 4 and 5, respectively). See SEQ. ID. NO: 15 and SEQ. ID. NO. 17, respectively. A vaccine vector was also developed employing "wild type" human DR5 as antigen, encompassing the extracellular, transmembrane, and intracellular domains (Example 2 and FIG. 2B, top figure, with vector details FIG. 6; and see SEQ. ID NO: 21 for nucleotide sequence and SEQ ID NO: 22 for deduced amino acid sequence of antigen). Additional human DR5 antigens encoding the extracellular and transmembrane domains of DR5, without and with td1, are given as SEQ. ID NO: 13 and SEQ. ID NO: 23, respectively. For deduced amino acid sequences see SEQ ID NO: 14 and SEQ ID NO: 24, respectively. The two vaccine vectors are also depicted in FIG. 2, bottom two figures, and in more detail in FIGS. 7 and 8. Alternatively, the polynucleotides of the present invention can be ligated into expression vectors known in the art to render suitable hosts to produce the desired peptides.

The genetic vaccine can be delivered to the host in a vehicle selected for optimum immunogenicity. In a preferred embodiment the vaccine is delivered in the form of a naked DNA plasmid. The DNA vaccines have important advantages. They can be administered more repeatedly, and for a longer period, than microbial vectors, which, containing foreign protein, rapidly elicit an immune response which eliminates the vectors before their genetic payload can be expressed. DNA vaccines are easily modified, can be produced in large quantity and at high purity, and are much more stable than peptide or proteinaceous vaccines.

Alternatively, the polynucleotides of the present invention may be packaged into a liposome or into various microbial vectors known in the art, including but not limited to retrovirus vectors, adenovirus vectors, vaccinia virus vectors, poxvirus vectors, adeno-associated virus vectors, lentivirus vectors, and virus like particles (Harrop et al., 2006). Attenuated bacterial vectors may also be employed, such as species of *Salmonella, Shigella, Listeria, Yersinia*, and *Escherichia* (Vassaux et al., 2006).

In the preferred vaccination regime, the pVAX vector is delivered as naked DNA by intramuscular injection followed by the delivery of an electric pulse, a strategy known as electrovaccination (Example 1). The experience of the inventors, as well as reports in the literature, show that electroporation significantly enhances DNA transfection efficiency in vivo (Widera et al., 2000). Alternatively, the vector containing the polynucleotide of the invention can be introduced in combination with protein or non-protein adjuvants that are known in the art for enhancing immune reactions. Moreover, agents such as protein carriers to enhance solubility and calcium ion to help the intracellular uptake of plasmids may be used in combination. Pharmaceutically acceptable agents that facilitate transfection may be combined as required.

The polynucleotide vaccine of the present invention can be administered by any alternative method, and at sufficient dose, to generate an immune response in a host. Appropriate methods include but are not limited to injections, or infusions via such parenteral routes as intravenous, intraperitoneal, subcutaneous, intradermal, or intramuscular. The vaccine may be coated onto microparticles such as gold particles and delivered to accessible tissues by biolistic bombardment, such as by a commercial gene gun. The vaccine may be incorporated into nanoparticles for delivery. The vaccine may be delivered to mucous membranes, for example by inhalation or via nasal instillation. Alternatively, it may be transfected or transduced ex vivo, into a cell population derived from a host, such as antigen presenting cells or other bone marrow derived cells. The cells are then returned to the host to provide expression of the vaccine in vivo. The vaccine can also be delivered as an edible vaccine.

The present invention can be employed in any type of host animal capable of generating specific antibodies to death receptors. Specific examples include mammals, such as mice, rats, bovines, pigs, companion animals such as dogs and cats, and primates such as monkey and human. Preferable host animals of the present invention include primates, particularly human.

The output of antibodies elicited by the vaccines of the present invention must be assayed in order to determine host response and optimal treatment regime. In a preferred embodiment, antibody output is measured by a dual fluorescence assay of the binding of host serum anti-DR5 antibodies to cells expressing DR5 in vitro. For example, a vector encoding mDR5-ectm-eGFP induced co-expression of surface DR5 and green fluorescent protein in the cells of the murine mammary tumor cell line D2F2. Sera of immunized and control animals were incubated with the cells, which were then washed and stained with red fluorescent secondary antibodies to mouse immunoglobulins. Binding of antibody was detected as the percentage of dual-labeled cells at a given dilution of serum, and by the intensity of the fluorescence (Example 1, FIG. 9D.) However, those skilled in the art can determine the progress of immunization by measuring the antibody titer by other assay methods including but not limited to Western blotting, ELISA, and ELISpot.

Figure 9:
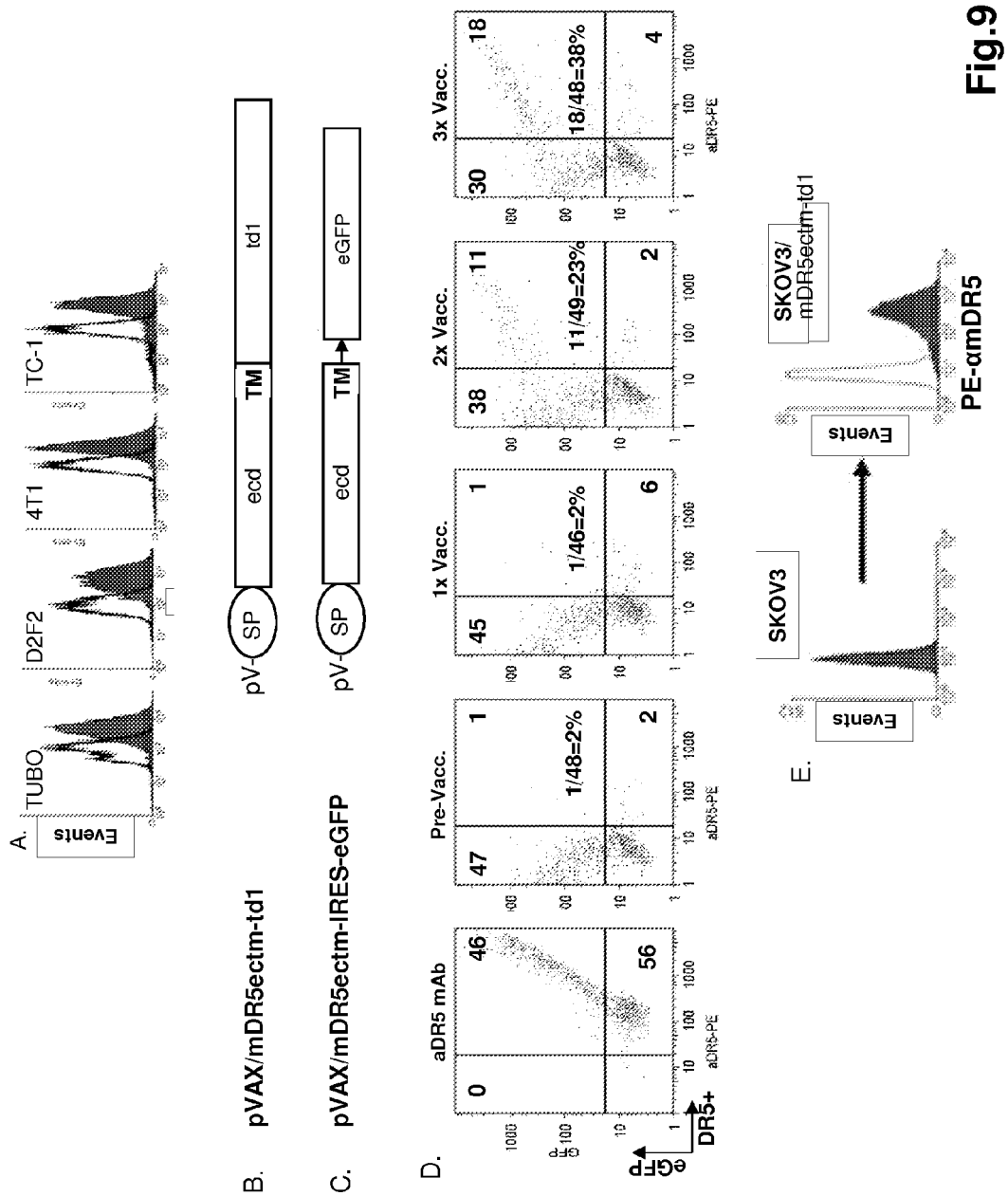

The humoral response to the vaccine of the present invention is polyclonal and will therefore likely consist of a mixture of antibodies with agonist or antagonist activity toward death receptors, as well as antibodies that bind death receptors without signaling effect. It is necessary to determine not only whether a given vaccine elicits antibodies, but also whether those antibodies are predominantly agonist. In a preferred embodiment, this is accomplished by measuring the apoptotic response of tumor cells expressing the targeted death receptor. A variety of murine and human tumor cell lines express DR5, as determined by staining with antibodies known to be specific for that receptor, including murine mammary tumor lines TUBO, D2F2, 4T1, the murine lung epithelial tumor line TC-1, and human breast carcinoma line MDA-MB231 (FIG. 9A). Alternatively, tumor cell lines may be transiently or stably transfected with genes encoding a death receptor for the purposes of assaying agonism by antibodies in the sera of immunized subjects.

Figure 11:
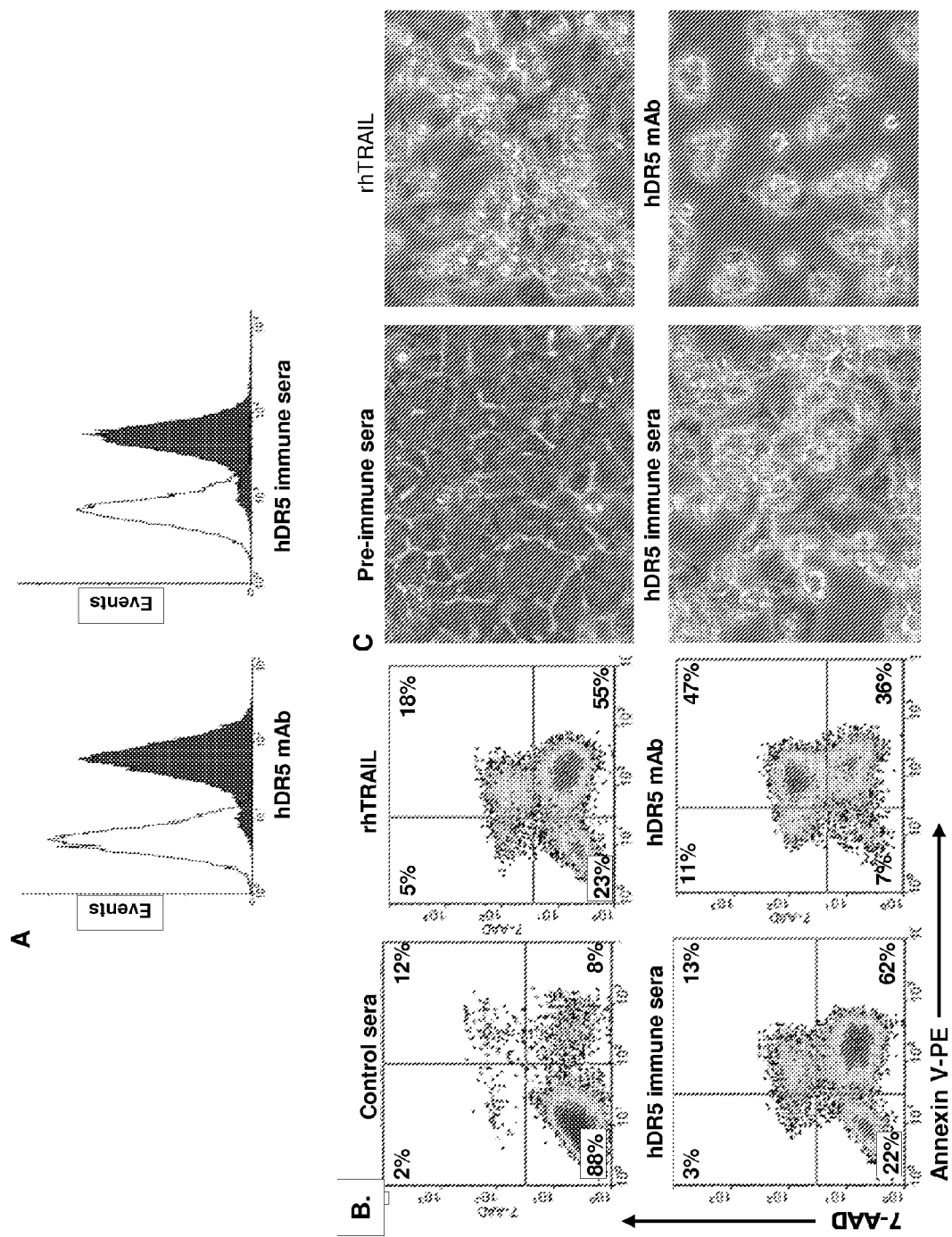

For example, mice are electrovaccinated with pVAX/hDR5, a vector encoding wild type human DR5, for four courses of bi-weekly treatments. Immune sera at a dilution of 1:20 were verified to bind MDA-MB231 breast carcinoma cells at levels comparable to that of a known monoclonal antibody to human DR5 (Example 2, FIG. 11A, compare "hDR5 immune sera" to "hDR5 mAb"). To measure apoptosis induction, human ovarian cancer line SKOV3 cells expressing DR5 were incubated with control or immune sera, followed by goat anti-mouse IgG-Fc for cross-linking. After overnight incubation in the presence of cyclohexamide, cell apoptosis was measured by staining with Annexin V-PE and 7-AAD. The percentage of positive cells demonstrates the induction of apoptosis by hDR5 immune sera (FIG. 11B). Induction of cell death may also be measured by the detection of other products expressed during apoptosis, such as cleaved (active) caspase 3, and by microscopic inspection of target cells for morphologies and behaviors typical of apoptosis, such as rounding and detachment. (FIG. 11C). Those skilled in the art will recognize that cell lines and apoptosis detection techniques will be selected according to the specific death receptor being targeted, and the species in which the response is desired.

The dosage and frequency of the death receptor vaccines of the present invention, and the nature of accompanying treatments, depends on the immunogenicity of the specific vaccine in the specific host. Those skilled in the art can determine the regime by administering a known dose of the composition into a test animal and measuring the antibody titer by assay methods such as ELISA, or by the binding of antibody to test cells as in the flow cytometric assays of Examples 1 and 2, or by measuring cytokines associated with humoral response. Those skilled in the art will recognize that the immunogenicity of a genetic vaccine depends in part on the effectiveness of the regulatory sequences, such as transcription and translation promoters, used in the expression vectors of the present invention. The dose of the vaccine can be adjusted based on the specific expression vector used.

A major variable in the effectiveness of a vaccine against a self antigen is the degree of tolerance which must be overcome. This tolerance is exerted mainly be natural Treg which develop in the thymus upon high affinity recognition of antigens in the thymic stroma (Colombo and Piconese, 2007). These cells are activated by engagement of their receptors by specific self antigen, but they exert nonspecific effects on nearby immune precursors and effectors. The effects are mainly produced by direct contact, via surface CTLA-4, membrane bound TGF-beta, or by the pericellular secretion of adenosine (Colombo and Piconese, 2007). These natural Treg are characterized by high constitutive expression of the IL-2 receptor CD25, CTLA-4, GITR, and the transcription factor FOXP3.

Another major variable in the effectiveness of a vaccine against self antigens, and indeed any vaccine, is the degree of immunosuppression encountered. Tumors tend to induce immuosuppression. This is mediated in part by adaptive subsets of Treg which arise in the periphery and exert effects mainly through soluble factors such as IL-10, IL-13, and TGF-beta (Mocellin et al, 2004). The development of these Treg is encouraged by defective antigen presentation. Antigens presented with incomplete or otherwise aberrant co-stimulation tend to induce the development of Treg (Martin-Orozco and Dong, 2007). Tumors encourage this aberrant antigen presentation through the production of such suppressive factors such as TGF-beta, prostaglandin E2, and IL-10. Many of these same factors exert direct suppressive effects upon immune precursors and effectors (Mocellin et al., 2004).

A preferred embodiment of the present invention illustrates an effective approach to overcoming tolerance to self antigens and tumor-induced immuosuppression. Antigen presentation was enhanced by the fusion of domains of the self antigen DR5 with the adjuvant td1, and further enhanced by GM-CSF expression rendered at the vaccination site. Tolerance was reduced by the depletion of Treg. BALB/c mice were depleted of regulatory T cells by infusion of anti-CD25 antibody, electrovaccinated 4 times with pVAX/mDR5ectm-td1 and a plasmid encoding GM-CSF (Example 1), and challenged s.c. with D2F2 mammary tumors which expressed endogenous mDR5. D2F2 tumors were rejected in 4 of 10 immunized mice (Example 1, FIG. 10). Immunization with control pVAX vector alone conferred no protection to seven of eight mice (FIG. 10), DNA encoding wild type mouse, rat or human DR5 provided no protection at all (not shown). In this example, tolerance to DR5 was overcome by the presentation of the DR5 antigen in fusion with td1, plus the stimulation of effective antigen presentation by local GM-CSF plus the temporary depletion of tolerance-mediating regulatory T cells. The result was the induction of death receptor agonist antibodies that protected against the formation of new tumors.

In light of the predictive nature of animal models in the development of vaccines, and in light of the strong structural and functional homology between mouse and human TRAIL receptors (Wu et al., 1999), the present invention will be effective against human tumors expressing death receptors, the same tumor types affected by existing monoclonal antibodies against DR4 and DR5 and by recombinant TRAIL. These tumors include, but are not limited to, colorectal, ovarian, breast, prostate, non-small cell lung, pancreatic, head and neck, and skin cancers and hematopoietic tumors such as lymphomas, multiple myeloma, and leukemias (Belyanskaya et al., 2007; Plummer et al., 2007).

In an exemplary clinical regime, the vaccine of the present invention is administered to breast cancer patients who have existing disease or are at risk of recurrence after such therapies as chemotherapy, hormonal therapy or radiotherapy, and monoclonal antibodies to the Her-2/neu antigen.

Figure 6:
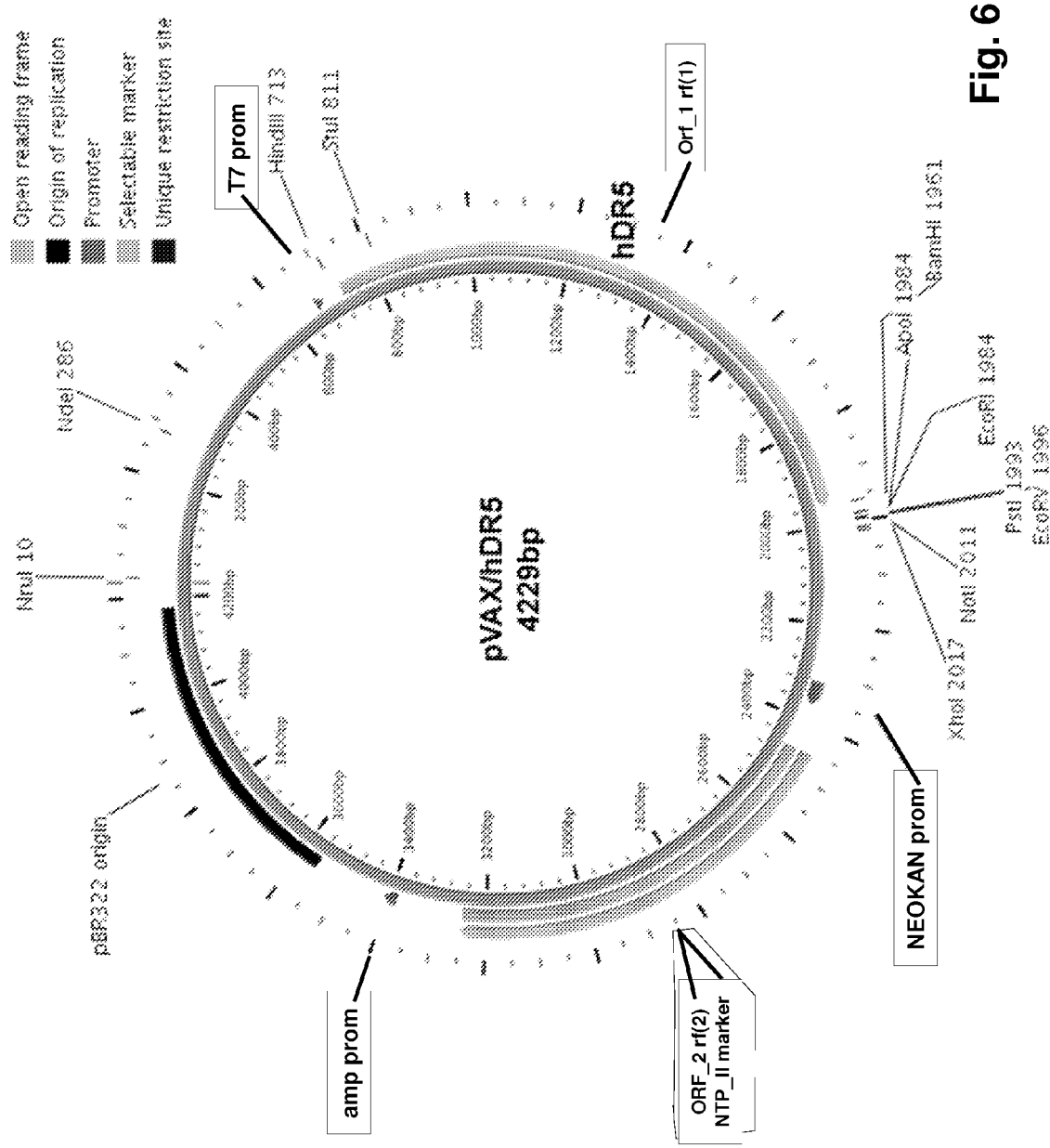

Patients receive injections with a naked DNA expression vector encoding wild type human DR5 (FIG. 6 and SEQ. ID NO: 21), although any of the DR4 and DR5 polypeptides and adjuvant polypeptides of the present invention may also be employed as determined by those of skill in the art of tumor immunotherapy. Injections are both intramuscular (i.m.) (270 μg of plasmid) into the deltoid region and intracutaneous (i.c.) (30 μg of plasmid). Optionally, injections of the GM-CSF protein (LEUCOMAX®, 40 μg) are given i.c. at the same location as the DNA vaccine injection. Alternatively, GM-CSF is delivered in the form of a DNA expression plasmid. Similar treatments with other enhancers of antigen presentation such interleukin-12 and IL-18, and other enhancers of immune response, such as interleukin-2 (e.g. PROLEUKIN®) can be added or substituted as deemed appropriate by those skilled in the art. Patients receive 5 cycles of immunization, with a typical cycle consisting of Day 1: 40 μg of GM-CSF i.c.

Day 2; 40 μg of GM-CSF i.c.

Day 3; 40 μg of GM-CSF i.c.

Day 4; 40 μg of GM-CSF i.c.

Day 5; 40 μg of GM-CSF i.c.

Day 3; 270 μg of hDR5 DNA plasmid i.m. and simultaneously 30 μg of hDR5 plasmid+40 μg of GM-CSF given i.c.

This schedule of immunizations is repeated 5 times at 4 week intervals. Regulatory T cells are temporarily depleted before the start of therapy by administration of ONTAK®, a conjugate of IL-2 and diphtheria toxin which binds to and kills a subset of regulatory T cells which mediates a large portion of tolerance to self antigens. A single intravenous dose of ONTAK® 2 (18 μg/kg) is administered 4 days prior to each vaccination cycle. Alternatively, the suppressive action of Treg may be blocked temporarily by antibodies which blockade CTLA4. This molecule is highly expressed on Treg subsets and it triggers inhibitory signals in other lymphocytes via binding to CD80 and CD86 (Cranmer and Hersh, 2007). For example, each vaccination can be accompanied by i.v. infusion of ipilimumab (MDX-10, Medarex Inc.), a humanized antibody which blockades CTLA-4. Infusions are of 1-3 mg/kg over 90 minutes. Infusions can be continued on a schedule of one every four weeks for 6 months, and one every 12 weeks for another six months (Sanderson et al., 2005). Another measure, which ameliorates both Treg-induced tolerance and many forms of tumor induced suppression, is the administration of the cytotoxic drug cyclosphosphamide, in a low dose, metronomic regime (Ghiringhelli et al., 2007). Another alternative is to employ antibodies to CD25 or other antibodies or other agents known in the art to deplete or inhibit the function of Treg.

Immunization against self antigens involves breaking tolerance and establishing a vigorous immune response. This requires a level of immunocompetence which may be lacking in individuals suffering from immunocompromising conditions such as cancer and the cytotoxic therapies used to treat that disease. The compositions and methods of the present invention may therefore be used to screen for candidates sufficiently immunocompetent to rise to the challenge of immunization against a self antigen. The antigens tested may be the same death receptor for which vaccination is contemplated, for example DR5. Alternatively, vaccination against DR5 may have utility as a standardized indirect indicator of ability to respond to any self antigen. This may be especially useful when treatment will employ tumor vaccines in which the antigen is delivered as cells or extracts of patient tumor, in which the actual antigens are both unknown, and difficult and expensive to prepare. The immunocompetence test of the present invention can be administered before any tumor excision and vaccine preparation is performed.

EXAMPLE 1

Anti mDR5 Vaccine Overcomes Tolerance and Induces Antideath Receptor Antibodies which Protect Against Tumor Development Tumor Cell Lines and Culture All tissue culture reagents were purchased from Invitrogen (Carlsbad, Calif.) unless otherwise specified. Cell lines were maintained in vitro in DMEM supplemented with 5% heat-inactivated cosmic calf serum (Hyclone, Logan, Utah), 5% heat-inactivated FBS (Sigma, St. Louis, Mo.), 10% NCTC 109 medium, 2 mM L-glutamine, 0.1 mM MEM non-essential amino acids, 100 units/ml penicillin, and 100 µg/ml streptomycin.

D2F2, a mouse mammary tumor line, was derived from a spontaneous mammary tumor that arose in the BALB/c hyperplastic alveolar nodule line D2 originally induced with prolactin (Mahoney et al., 1985). Line 4T1 was derived from a spontaneous mammary tumor that arose in a female BALB/cfC3H mouse which was a BALB/c mouse infected with mouse mammary tumor virus MMTV(C3H) (Miller et al., 2004). The TUBO cell line provided by Dr. Guido Formi (Torino, Italy), was derived from a spontaneous mammary tumor which arose in a BALB NeuT transgenic mouse expressing a transforming rat neu oncogene (Luchini et al, 1992; Rovero et al., 2000). TUBO cells grow progressively in normal BALB/c mice and give rise to tumors which are histologically similar to spontaneous mammary tumors of BALB NeuT mice. C57BL/6 TC-1 cell line provided by Dr. T. C. Wu, The Johns Hopkins University, Baltimore, Md. was derived by transforming lung epithelial cells with human papilloma virus-16 E6, E7 and ras oncogene (Lin et al., 1996). All of the above lines were found to express surface DR5 as determined by staining with MD5-1, an anti-DR5 monoclonal antibody (FIG. 9A). SKOV3 (ATCC No. HTB-77), a human ovarian carcinoma line, expresses human DR4 and DR5.

Construction of mDR5 Vaccine

Mouse DR5DNA vaccine pVAX/DR5ectm was constructed to encode the extracellular (ecd) and transmembrane (tm) domains (SEQ. NO: 11). pVAX/DR5ectm was further modified to become pVAX/DR5ectm-td1 by fusing tetanus toxin fragment C domain 1, the immunogenic but non-toxic peptide, after the tm region to increase the immunogenicity of mDR5 (FIGS. 4 and 9B, SEQ. NO:15). Tetanus toxin fragment C domain 1 (td1) acts as an adjuvant to potentiate the immune response to the vaccine antigen.

Construction of pVAX/mDR5ectm. mDR5 cDNA (Accession #NM_020275) was subcloned between the HindIII and KpnI sites in the MCS (Multiple Cloning Site) of pVAX1 to yield the vector pVAX/mDR5. The 505 bp BamHI/BamHI fragment in pVAX/mDR5 was replaced by the self-annealed 20-base DNA duplex with BamHI sticky ends as described for pVAX/mDR5-eGFP below. This deleted the 3'-terminal 160 codons of the mDR5 icd, which contains the Conserved Death Domain (CDD) and stop codon. The DNA duplex added an inframe stop codon at the 3' end, leaving 20 codons of the icd adjacent to the tm domain.

Construction of pVAX/mDR5ectm-td1. A cut-and-splice method was used to fuse humanized td1 (Tetanus Toxin C domain) to the 3' end of mDR5ectm. First, pVAX/mDR5 was cut with BamHI and XbaI. This removed the 3' terminal 160 codons of the icd and stop codon from mDR5 as detailed above. The remainder of the BamHI/XbaI-restricted vector was then ligated to the 795 bp BamHI/XbaI fragment from pVAX/td1, which contains 24 bp of the 5' UTR (UnTranslated Region) plus the entire open reading frame of td1 plus its stop codon. The resulting vaccine construct expresses mDR5ectm-td1, which by design lacks the CDD region of DR5 to eliminate its proapoptotic activity. (Note that the fusion product contains 6 additional bridge codons (coding for LVQCGG), amino acids 222-227 of SEQ ID NO: 16) between mDR5ectm and td1 that are contributed by the 5' UTR of the td1 expression vector (SEQ ID NO: 15, SEQ ID NO: 16)).

Vaccination Procedure

Mice were injected in the quadriceps muscle with 50 µg of anti-DR5 DNA vaccine and 50 µg of pEFBos/GM-CSF in a total volume of 50 µl, using a tuberculin syringe with a 271/2 gauge needle. The site of injection was shaved and wiped with 70% alcohol before DNA injection. Use of granulocyte-monocyte colony-stimulating factor (GM-CSF) can augment immune response. Therefore, pEFBos/GM-CSF, encoding murine GM-CSF provided by Dr. Nishisaki, Osaka University, Osaka, Japan was included in the vaccine formula. DNA injection was followed immediately by square wave electroporation at the site of injection using a BTX830 (BTX Harvard Apparatus, Holliston, Mass.). A tweezer electrode was used to deliver eight pulses at 100V for 20 msec per pulse. The tweezer electrode was switched to the reverse direction after 4 pulses. Vaccination was repeated 2-4 times at 2 wk intervals.

In some experiments mice were injected i.p. with 0.4-0.5 mg anti-CD25 mAb, PC61, to deplete CD4$^+$CD25$^{hi}$ regulatory T cells (Treg). At 7-10 days after Treg depletion, mice were injected in the quadriceps muscle with 50 µg pVAXmDR5ectm-td1 and 50 µg pEFBos/GM-CSF in a total volume of 50 µl, followed by electroporation at the injection site, as described above.

Assay to Detect Production of Anti-DR5 Antibody.

Figure 5:
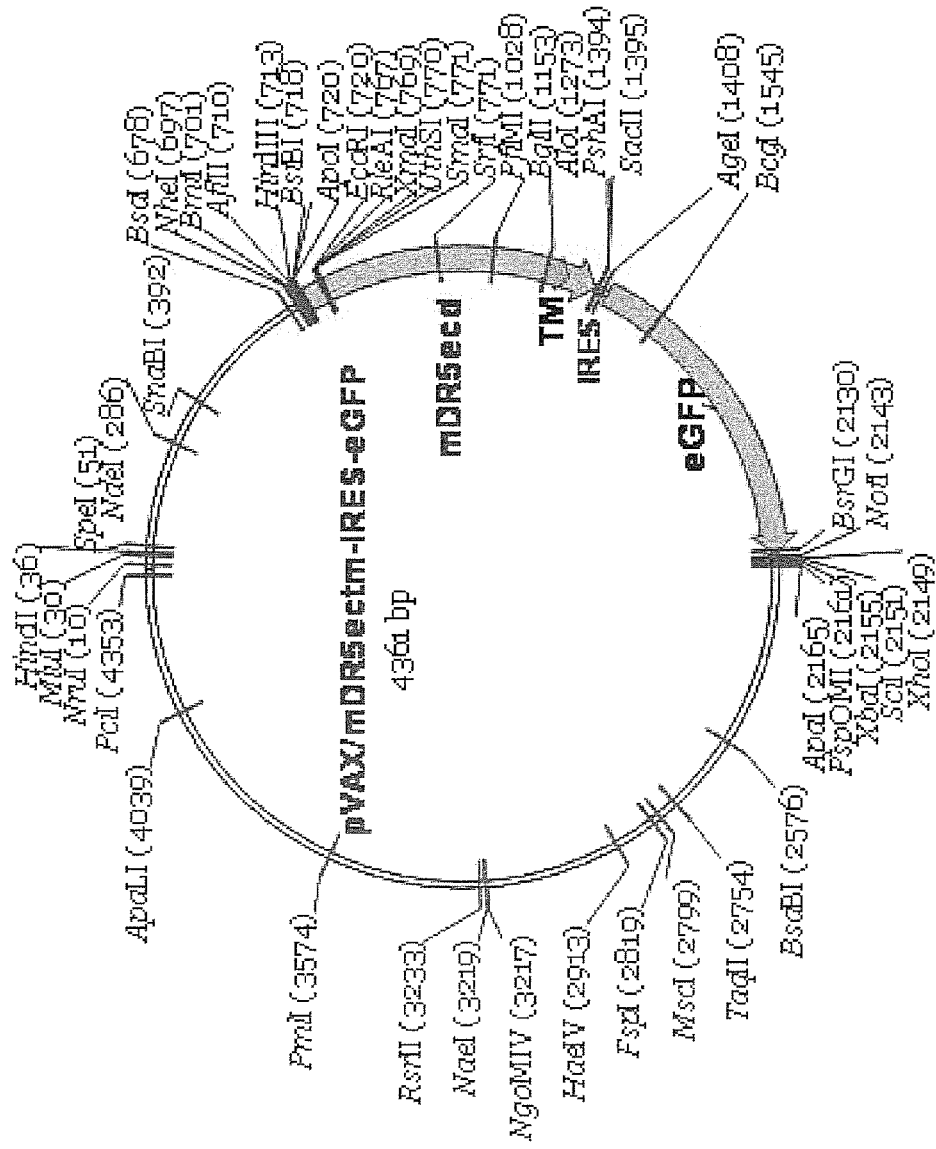

To provide a sensitive assay for detecting anti-DR5 antibody, pVAX/mDR5ectm-IRES-eGFP was constructed to express both mDR5 and eGFP (FIGS. 5 and 9C, SEQ. NO: 17). pVAX/mDR5ectm-IRES-eGFP was constructed from pVAX/mDR5-IRES-eGFP.

Figure 3:
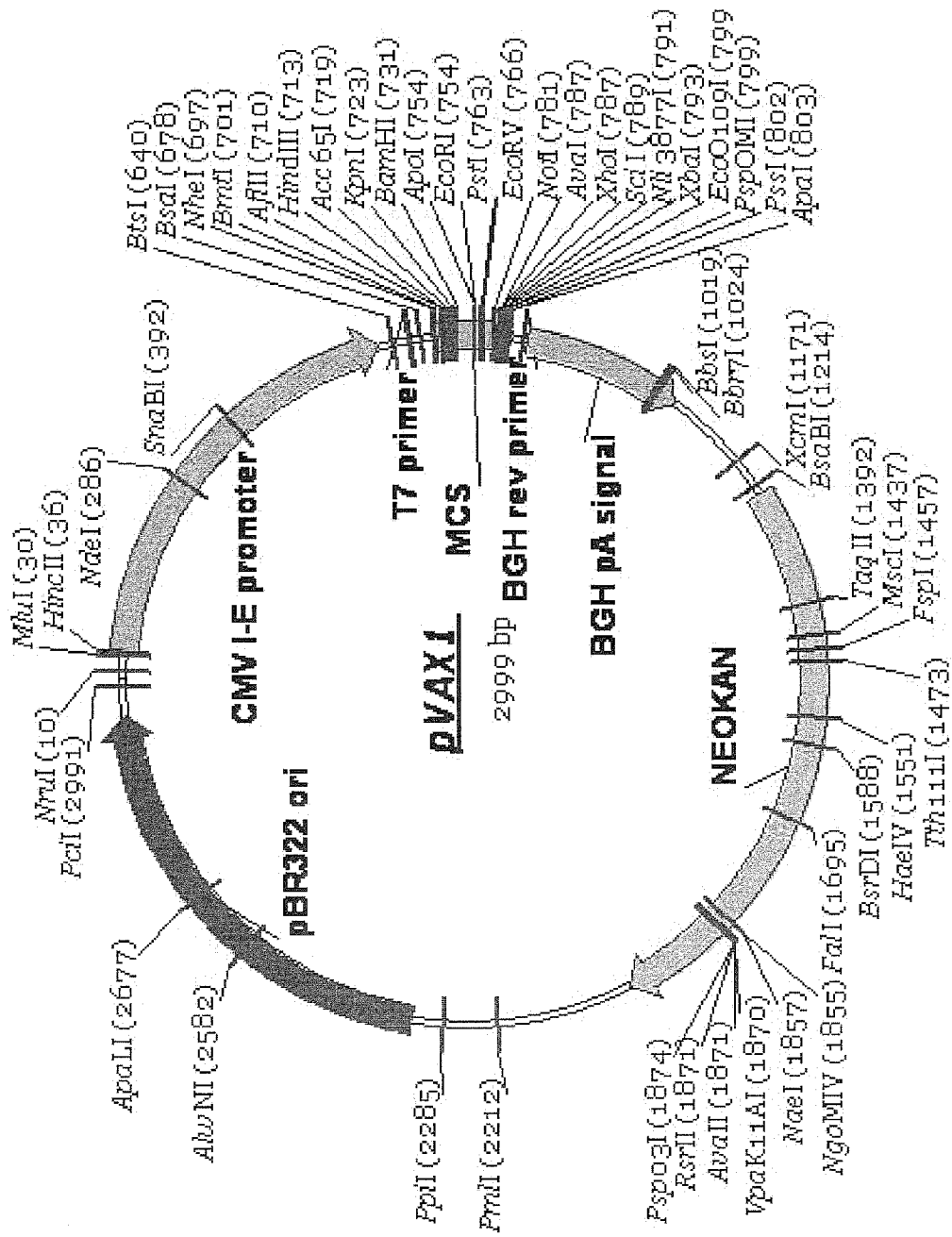
Figure 4:
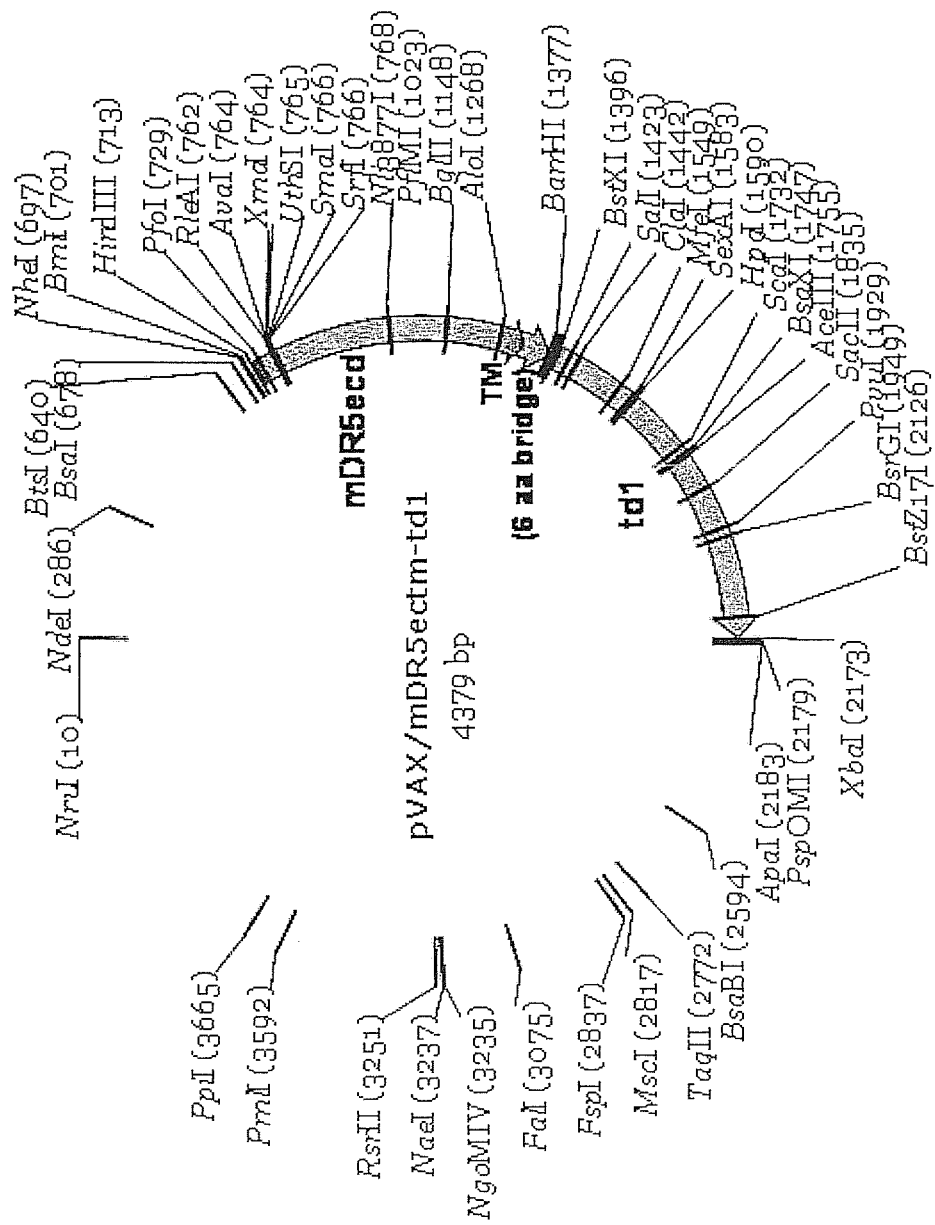

Construction of pVAX/mDR5-IRES-eGFP: mDR5 cDNA (Accession #NM_020275) was subcloned between the HindIII and KpnI sites in the MCS (Multiple Cloning Site) of pVAX1. eGFP cDNA, preceded by an IRES (Independent Ribosome Entry Site), was then cloned downstream of stop codon of mDR5, between the KpnI & NotI sites, to give the vector pVAX/mDR5-IRES-eGFP. mDR5 and eGFP are independently translated from a bicistronic transcript initiated from the human CMV immediate-early promoter in pVAX1 (FIG. 3).

To eliminate pro-apoptotic activity of mDR5, the CDD was deleted from the icd of full-length mDR5. For this, pVAX/mDR5-IRES-eGFP was cut with BamHI, which released a 505 bp BamHI/BamHI fragment spanning the 3' terminal 160 codons of mDR5, including the CDD and stop codon. This fragment was replaced with a 20-base internally-palindromic oligodeoxynucleotide that forms a duplex with BamHI sticky ends, and contains an inframe stop codon (5'-GATCG GTGAC CGCGG TCACC, nucleic acids 658-677 of SEQ ID NO: 17). (Note that the original BamHI sites are eliminated by this duplex oligo to facilitate screening of derivative clones of interest.) This gave pVAX/mDR5ectm-IRES-eGFP from which the CDD has been entirely deleted, leaving only 20 codons of the icd immediately following the TM domain (as indicated in FIG. 5 and SEQ NO: 17). pVAX/mDR5ectm-IRES-eGFP independently expresses mDR5ectm and full-length eGFP.

Cells of murine mammary tumor cell line D2F2 were transfected with pVAX/mDR5ectm-IRES-eGFP as described for SKOV3 cells, below. Sera of immunized and control mice were incubated with the cells, which were then washed and stained with red fluorescent secondary antibodies to mouse immunoglobulins.

Binding of antibody to DR5 was detected as the percentage of all green fluorescent cells that were also red fluorescent (FIG. 9D.) As a positive control, cells were incubated with a known antibody to DR5, MD5-1, supplied by Dr. Hideo Yagita (Juntendo University, Tokyo, Japan) (FIG. 9D, left hand panel).

In experiments with human ovarian cancer cell line SKOV3 transfected to express mDR5ectm-td1, single fluorescence staining with MD5-1 was employed. SKOV3/mDR5ectm-td1 cells were generated by co-transfecting human SKOV3 cells with pVAX/mDR5ectm-td1 and pMSCV/puro (Clontech, Palo Alto, Calif.). Cells overexpressing mDR5ectm-td1 were sorted by flow-cytometry using FACS Vantage SE/DiVa SORP (BD Biosciences, San Jose, Calif.), followed by single cell cloning. Transfected cells were maintained in DMEM supplemented with 10% heat-inactivated cosmic calf serum, 10 units/ml penicillin/streptomycin, and 3 µg/mL puromycin. Flow cytometric analysis was performed with a FACSCalibur (Becton Dickinson, Mountain View, Calif.).

In vivo Tumor Prophylaxis Assay

To measure in vivo anti-tumor activity of the pVAX/mDRectm-td1 vaccine, BALB/c mice were depleted of regulatory T cells (Treg) as described above. Mice were electrovaccinated with pVAX/mDRectm-td1 four times, once every two weeks, as described above. They were then challenged s.c. with D2F2 mammary tumors which expressed endogenous mDR5. Tumor growth was monitored weekly by palpation.

Results

Vaccination with pmDR5-td1 Induces Anti-DR5 Antibodies.

Mice were electrovaccinated with pVAX/mDRectm-td1 as described above, or with control plasmids encoding mDR5ectm without td1. Sera were collected after one, two, and three vaccinations. Sera were assayed for DR5 binding antibodies by incubation with D2F2 cells transiently transfected with pVAX/mDR5-IRES-eGFP. As described above, bound antibody was detected by binding of red fluorescent anti-mouse-Ig, and therefore binding of serum antibodies to DR5 was detected as dual red/green cellular fluorescence representing cells both expressing DR5 and binding anti-DR5 (FIG. 9D). In a positive control, cells were incubated with a known antibody to DR5 rather than with test sera FIG. 9D (first panel from left). It may be seen that in this positive control, approximately 46%, of cells expressed DR5 and of these, all bound anti-DR5 (upper right hand quadrant, dual fluorescence). In contrast, when the cells were exposed to pre-immune serum (second panel from left), there was little anti-DR5 reaction. Of all cells expressing DR5 (all green fluorescence left and right upper quadrants, 48% of cells), only 2% were dual fluorescent (upper right panel). After two more courses of vaccination, however, the percentage of DR5 expressing cells binding anti-DR5 increased to 38% (right hand panel, 18% dual fluorescent cells/48% green fluorescent cells). Vaccination with DNA encoding wild type mouse, rat, or human DR5 did not induce Ab that recognized mouse DR5 (not shown).

The specificity of the induced antibodies was further demonstrated in experiments with the human ovarian carcinoma cell line SKOV3, which expresses endogenous human DR5 on its surface. Serum of immunized mice did not stain SKO3 transfected with a control vector, but stained nearly 100% of SKOV3 transfected with pVAX/mDR5ectm-td1 (FIG. 9E).

This is further evidence that the anti-DR5 antibodies induced in mice by pVAX/mDR5ectm-td1 vaccine bind specifically to the immunizing antigen, and not to even a closely related antigen, in this case human DR5.

Taken together, the results prove the principle that tolerance to death receptor self antigens can be broken, and death receptor antibodies can be produced, through the use of a genetic vaccine, in this case a vaccine encoding hybrid polypeptides of the DR5 and td1.

Antibodies Induced by pVAX/mDR5ectm-td1 Protect Mice from Subsequent Tumor Challenge.

Figure 10:
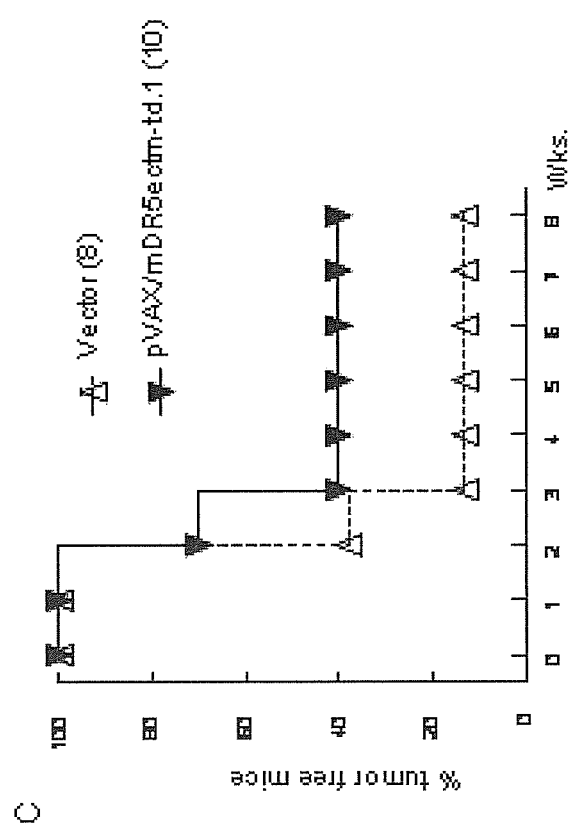

BALB/c mice were depleted of regulatory T cells by treatment with anti-CD25 as described above, electrovaccinated 4 times with pVAX/mDR5ectm-td1 and pGM-CSF as described above, and challenged s.c. with D2F2 mammary tumors which expressed endogenous mDR5. D2F2 tumors were rejected in four of ten immunized mice (FIG. 10). Of eight animals immunized with control pVAX vector, seven developed tumors (FIG. 10). DNA encoding wild type mouse, rat or human DR5 also gave no protection (not shown).

The results prove the principle that tolerance to death receptor self antigens can be broken, to produce antibodies that provide prophylaxis, that is, the prevention of initiation of new nests of tumor. In light of the predominantly agonist nature of antibodies induced by TRAIL receptor vaccines in Example II, below, it is most likely that the prophylactic effect was caused by the triggering of DR5 on the D2F2 cells. No unfavorable side effects were observed for the entire 8 week course following tumor challenge. The animal prophylaxis model is highly predictive of the ability of a treatment to prevent metastasis and recurrence of primary tumor after surgery, chemotherapy, and other acute treatment modalities: and also of the ability of a treatment to prevent cancer in individuals at high risk of carcinogenesis.

EXAMPLE 2

Anti Human DR5 Vaccine Induces Predominantly Agonistic Ab Against DR5

Construction and Use of pVAX/hDR5.

Full length wild type human DR5 (SEQ ID NO: 21; deduced amino acid sequence SEQ ID NO: 22) was used as the antigen in the vaccine vector pVAX/hDR5 depicted in FIG. 2B and FIG. 6. The 1446 nucleotide open reading frame (ORF) of human DR5 isoform 2 cDNA was PCR amplified from cloned DR5 cDNA (Accession #NM__147187). The 5' PCR primer contained a HindIII site and a Kozak consensus ribosome binding site (RBS; GCG ACC ATG G). The 3' primer contained a BamHI site. The forward PCR primer (h3k-hDR5-f) is: 5'-ATATC TACAA GCTTG CGACC ATGGA ACAAC GGGGA CAGA (SEQ ID NO: 27). The reverse primer (bam-hDR5-r) is: 5'-CTAGA TGGAT CCTTA GGACA TGGCA GAGTC TGC (SEQ ID NO: 28). The 1450 bp PCR product, which contained the full-length DR5 orf with its original start and stop codons, was digested with HindIII and BamHI, then directionally cloned into the HindIII/BamHI sites of pVAX1.

pVAX/hDR5ectm (FIG. 7) was also constructed from the full-length human DR5 isoform 2 orf (Accession #NM__147187). Human DR5 cDNA was PCR amplified with a 5' primer containing a HindIII site and Kozak RBS as before. The 3' reverse primer was homologous to codons 168-170 of DR5, and introduced a stop codon plus a BamHI site at the 3' end. The forward PCR primer (h3k-hDR5-f) is: 5'-ATATC TACAA GCTTG CGACC ATGGA ACAAC GGGGA CAGA (SEQ ID NO: 27). The reverse primer (b-hDR5ect-r) is: 5'-CTAGA TGGAT CCTCA GCCTC CACCT GAGCA GATG (SEQ ID NO: 29). (Note that in primer b-hDR5ect-r, alternate codon choice was used for two gly residues as underlined. These facilitate PCR amplification while maintaining the native amino acid sequence of the recombinant human DR5.) The 690 PCR product contains the 5' HindIII site/RBS and natural DR5 start codon, full-length signal peptide sequence, ecd, TM domain plus 19 codons of a truncated intracellular domain, followed by the stop codon and BamHI site. This was digested with HindIII and BamHI, then cloned into the HindIII/BamHI sites of pVAX1 as before.

pVAX/hDR5ectm-td1 (FIG. 8) contained DR5ectm fused to td1. DR5ectm was constructed by PCR as before, but with a 3' PCR primer terminating at codon 170 of mature human DR5, without a stop codon or added restriction site. This left a 19 codon fragment of truncated DR5 icd as in DR5ectm. The forward PCR primer (h3k-hDR5-f) is: 5'-ATATC TACAA GCTTG CGACC ATGGA ACAAC GGGGA CAGA (SEQ ID NO: 27). The reverse primer (td/hDR5ect-r) is: CCAAC AATCA AGGTT TTTGC CTCCA CCTGA GCAGA T (SEQ ID NO: 30), which codes for codons 165 through 170 of mature human DR5, plus codons 2 through 7 of humanized td1. Td1 was PCR amplified with a 5' PCR primer homologous to codons 2-7 of humanized td1 (which contains a novel added methionine codon at the 5' end of td1 for stand-alone expression in mammalian cells). The 3' PCR reverse primer is homologous to the terminal codon and stop codon of td1, and adds a BamHI site. The forward PCR primer (hect/Td1-f) is: 5' GTGGA GGCAA AAACC TTGAT TGTTG G (SEQ ID NO: 31). The reverse PCR primer (td/hect-r) is: 5'-CTAGA TGGAT CCTCA CAGCG GGTTA CCCCA GAAG (SEQ ID NO: 32). The 5' end of PCR amplified td1 was fused in reading frame to the 3' end of DR5ectm by overlap-extension PCR, giving an 800 bp product coding for the DR5ectm-td1 fusion product. This was digested with HindIII and BamHI, then cloned into the HindIII/BamHI sites of pVAX1 as before.

Vaccination of mice was performed as in Example 1.

Assay of Presence and Apoptotic Effect of Serum Antibodies.

Human tumor cell lines were subcultured in 6 or 12-well culture plates until 70-80% confluence. Media was replaced and supplemented with 0-5 µg/mL cyclohexamide. Human test cells were treated with various dilutions of experimental or control mouse serum, or with the positive controls 0-1 µg/mL human DR5 agonist mAb (clone 71903, MAB631; R&D Systems, Inc.) or 0-1 µg/mL recombinant TRAIL alone. Cells were incubated for an additional 20-24 hours prior to the evaluation of apoptosis by Annexin V staining and activated caspase-3 detection assays. Substitution or addition of different inhibitors and antibodies or immune sera were incorporated into this basic assay platform.

Apoptotic activity was measured with the Annexin V-PE Apoptosis Detection Kit I with 7-AAD (cat#559763; BD Biosciences Pharmingen™). Cells were harvested and equilibrated in binding buffer and reacted with PE-labeled Annexin V for detection of membrane phosphatidylserines that were exposed by apoptosis and the vital dye 7-AAD to detect dead cells. Stained samples were placed on ice and evaluated immediately by flow cytometry using the dual-color laser option (FL2 v. FL3) in a Becton Dickinson FACSCalibur flow cytometer. At least 10,000-20,000 events were collected for every sample. Data were analyzed using WinMDI version 2.8 software and plotted as four-quadrant, annexin V-PE versus 7-AAD, density plots to show the distribution of the: 1) live, non-apoptotic cells, 2) live apoptotic (annexin V-PE positive) cells, 3) the nonviable (7-AAD positive population) and 4) the nonviable late apoptotic cells (annexin V-PE and 7-AAD positive). Apoptotic activity was also measured by the presence of the cleaved (active) form of caspase 3. The flow cytometric assay was performed according to the manufacturer's recommendation using PE-conjugated rabbit monoclonal active caspase-3 antibody apoptosis kit from BD Pharmingen (#550914).

Results

Vaccination with pVAX/hDR5 Induces Predominantly Agonist, Apoptosis-inducing Antibodies Against Human DR5.

The serum of immunized mice contained anti-human DR5 antibodies, as detected by fluorescence assay of serum-incubated MDA-MB231, a breast carcinoma cell line which overexpresses DR5. At a serum dilution of 1:20, over 95% of the cells stained, relative to isotype control (FIG. 11A lower panel), a result nearly identical to that obtained with a known agonist monoclonal antibody to human DR5 (FIG. 11A, upper panel).

Over 70% of cells treated with immune serum showed staining by either annexin V alone (early apoptosis) or dual annexin-V 7-AAD staining (late apoptosis) (FIG. 11B. lower left panel). This was comparable to apoptosis induction by recombinant human TRAIL and a known agonist mAb (FIG. 11B, right hand panels). In contrast, only 20% of cells treated with preimmune serum were apoptotic. Induction of cell death was verified by typical apoptotic changes in cell morphology and cell detachment in monolayer cultures of SKOV3. These changes were observed in wells treated with immune sera, and to the same extent in wells treated with positive controls rhTRAIL and agonist mAb (FIG. 11C). Cells in wells treated with preimmune serum showed only occasional apoptotic figures (FIG. 11C).

The results show that despite the polyclonal nature of the humoral response to an anti-death receptor vaccine, vaccines inducing predominantly agonist antibodies can readily be selected.

EXAMPLE 3

Vaccination with Anti-hDR5 Induces Anti-hDR5 Antibodies which Cause Growth Inhibition and Apoptosis in Human Treatment-resistant Breast Cancer Cells, Effects which are Amplified by Cross Linking and by TRAIL In 15-20% of breast cancer patients, the tumors express neither estrogen receptor (ER) nor progesterone receptor (PR) nor Her-2. Patients with these triple negative breast cancers (TNBC) do not have the option of hormone or molecularly targeted therapy after they receive conventional treatment. However, these treatment resistant TNBC have been reported to be uniquely sensitive to extrinsic apoptosis (Rahman et al., 2008). We now show that lines of human TNBC cells are susceptible to the effects of anti-DR5 antibodies induced by vaccination.

Mice, Cell Lines and Reagents

BALB/c and SCID (age 6-8 weeks) female mice were purchased from Charles River Laboratory (Frederick, Md.).

Tissue culture reagents and cell line maintenance were as previously reported (Wei et al., 2005). Antigen presenting cells (APC) 3T3/KB and 3T3/DKB were generated in our lab (Wei et al., 2005). Briefly, BALB/c NIH 3T3 fibroblasts were transfected with Kd and B7.1 (KB), or with Kd, B7.1 and hDR5 (DKB). Stable clones were selected, and maintained in medium supplemented with 0.8 mg/ml G418 and 7.5 µg/ml of puromycin. Surface expression of hDR5 was confirmed by flow cytometry using monoclonal antibody (mAb) HS201 to human TRAIL-R2 or PE-conjugated DJR2-4 (eBioscience, San Diego, Calif.) and detected with phycoerythrin (PE) conjugated secondary antibodies (Jackson ImmunoResearch, West Grove, Pa.). Normal mouse serum or isotype matched mAb was the negative control. SUM159 and SUM149 cells were originally isolated from a primary human breast tumor at the University of Michigan, characterized and made available to us by Dr. Stephen Ethier (now at our institution) and maintained in RPMI+5% FBS 5 µg/mL Insulin and 1 µg/mL hydrocortisone. SUM159 and SUM149 are also available from Asterand, plc., Detroit, Mich.). MDA-MB231, BT-474 and SKBR3 were obtained from the ATCC (Manasas, Va.) and maintained in the recommended culture media. Human T cells were obtained from peripheral blood, enriched and activated in the presence of 20 ng/mL OKT3 (monoclonal antibody to human CD3, ORTHOCLONE by JOM Pharmaceutical Services, Inc., Shepherdsville, Ky.) and 100 U/mL human IL-2 (PROLEUKIN by Novartis, Karmanos Cancer Institute Hospital Pharmacy) in RPMI media supplemented with 10% Fetal Bovine Serum. IL-2 was replenished every two days.

DNA Immunization pCEP4 hDR5 encoding the full length human DR5 (SEQ. ID NO: 21) and pCEP4 hDR5 mut encoding human DR5 with a premature termination signal in the death domain (aa. 338) have been described (Pai et al., 1998). Coding sequences were obtained by restriction with BamHI and HindIII and sub-cloned using the equivalent sites of pVax-1, giving rise to pVax-hDR5 (WT) and pVax-hDR5 del (▲). pVax-hDR5 ECD-TM (ECTM), encoding the extracellular domain and transmembrane regions of DR5 (aa. 1-223) (SEQ ID NO: 13) was obtained by PCR amplification using the wildtype sequence as template and primers: Upper 5'-AT ATC TAC AAG CTT GCG ACC ATG GAA CAA CGG GGA CAG A-3' (SEQ ID NO: 25) and Lower 3'-GTA GAC GAG TCC ACC TCC GAC TCC TAG GTA GAT C-5' (SEQ ID NO: 26) and cloning into BamHI and HindIII of pVax-1.

pEFBos/GMCSF (pGM-CSF) encoding murine GMCSF was provided by Dr. N. Nishisaki at Osaka University, Osaka, Japan. pCD40LT encoding murine CD40 ligand Trimer was provided by Dr. Ralph Reisfeld at Scripps Research Institute, La Jolla, Calif. Mice were injected in the quadriceps muscle with plasmid DNA followed immediately by square wave electroporation over the injection site using a BTX830 (BTX Harvard Apparatus, Holliston, Mass.) as previously described (Wei et al., 1999; Jacob et al., 2006).

Measurement of Anti-hDR5 Antibody by Elisa

Human hDR5/Fc chimeric protein encoding aa 1-182 of the extracellular domain (EXBIO Antibodies, Cat No. RL-002-C050; Praha, Czech Republic) of human DR5 and the Fc portion of human IgG1 was immobilized to Immulon 2HB flat-bottom Elisa plates buy capture with goat anti-human IgG. Serum samples from control and phDR5 immunized mice were tested at 1:10,000-1:100,000 dilution and compared to a standard curve generated using mouse agonist monoclonal antibody MAB631 (R&D Systems, Minneapolis, Minn.). After 1 h incubation at RT, bound mouse IgG was detected with goat anti-mouse IgG HRP and developed with TMB Substrate Set (BD Biosciences, San Diego, Calif.). Reactions were terminated with 1 M Phosphoric Acid and OD read at 450-590 nm. The concentration of hDR5 specific IgG was calculated by linear regression based on the standard curve following background subtraction and corrected for the dilution factor to be expressed as µg/mL. Differences in antibody concentration were analyzed by the Student's t test.

Measurement of IFN-γ Secreting T Cells by ELISPOT Assay

A total of 5×10⁵ immune spleen cells were incubated with APC, 3T3/DKB cells or 3T3/KB cells as control at spleen cells to APC ratio of 10:1. IFN-γ. Elispots were measured as we previously described (Jacob et al., 2006) and the results expressed as the number of cytokine producing cells per 10⁶ cells. Data were analyzed using the Student's t test.

Cell Proliferation Assay

Cell proliferation was measured indirectly by mitochondria metabolic activity using a modified MTT (3-(4,5-dimethylthiazol-2-yl)-2,5-diphenyl tetrasodium bromide) assay (Mosman, 1983). SUM159 cells at 400,000 per mL were treated with a 1:50 final dilution of immune sera from vaccinated animals. A total of 50,000 cells in 125 microliters were plated. As controls, cells were treated with media alone or graded doses of DR5 agonist monoclonal antibody (mAb) mAb631 (R&D Systems, clone 71903, Minneapolis, Minn.) or recombinant TRAIL (BIOMOL, San Diego, Calif.). Approximately 20-24 hours after plating, 12.5 µl of 5 mg/ml MTT in PBS was added and incubated for 4 h at 37° C. before the stop reagent (Isopropanol with 0.04N HCl) was added and the absorbance measured at 600-650 nm. Activated T cells were treated in a similar fashion and proliferative activity assayed over three days using Alamar Blue™ (InVitrogen, Carlsbad, Calif.) according to the manufacture's specifications.

Apoptosis Assay

Cells were subcultured in 12- or 6-well plates until 70-80% confluence at which time media was replaced and immune or control serum added to achieve 0.5-2% final concentration. Media alone or known concentrations of agonist MAB631 or TRAIL were used as controls. After 20-24 h incubation cells were stained with Annexin V-PE+7-AAD using Annexin V-PE Apoptosis Detection Kit I with 7-AAD (cat#559763; BD Biosciences Pharmingen™). In some instances, immune sera or antibody was removed 30 minutes after incubation, washed once and either goat-anti-mouse IgG (10 µg/mL), or TRAIL (1 µg/mL) was added to induce receptor cross-linking. Stained samples were placed on ice and evaluated immediately by flow cytometry. Data were analyzed using WinMDI version 2.8 and plotted as four-quadrant, annexin V-PE versus 7-AAD, density plots to show the distribution of the: 1) live, non-apoptotic cells, 2) live apoptotic (annexin V-PE positive) cells, 3) the nonviable (7-AAD positive population) and 4) the nonviable late apoptotic cells (annexin V-PE and 7-AAD positive).

Caspase 3 and PARP Detection by Western Blot Analysis

SUM159 cells at 90% confluence were incubated for 5 hours with non-immune or hDR5 immune sera (1:50) or 5 µg/mL mAb631. In some instances cells were pretreated with 20 µM caspase-8 inhibitor Z-IETD-FMK (BD Pharmingen, San Diego, Calif.) or diluent (DMSO) for 30 minutes prior to and throughout the incubation with immune sera/antibodies. Whole cell lysates were extracted using 1× Cell Lysis Buffer (#9803, Cell Signaling Technology (Beverly, Mass.) as recommended by the manufacture's protocol. Equal amounts of proteins were resolved in 4-20% gels PAGEr Duramide® Gels (Cambrex, Rockland, Me.) and electro transferred to Immobilon-P (Millipore, Bedford, Mass.) PVDF membranes. Blots were probed overnight with primary antibodies and detected with Peroxidase-conjugated AffiniPure Goat Anti-Mouse (cat#115-035-071) or Goat Anti-Rabbit (cat#111-035-046) secondary antibodies from Jackson ImmunoResearch Laboratories. Blots were developed with enhanced SuperSignal☐ West Pico Chemiluminescent Substrate (Pierce Biotechnology, Inc.; Rockford, Ill.) and imaged with Kodak-MR film. Antibodies used for Western blot detection included, mouse monoclonal against cleaved PARP (Zymed, Carlsbad, Calif.), rabbit monoclonal against cleaved caspase3 (Asp175 (5A1) #9664, Cell Signaling Technology (Beverly, Mass.) or mouse ascites against B-actin (Sigma, St. Louis, Mo.).

Results hDR5 Immune Sera Bind to and Suppress the Growth of SUM159 TNBC Cells

Figure 12:
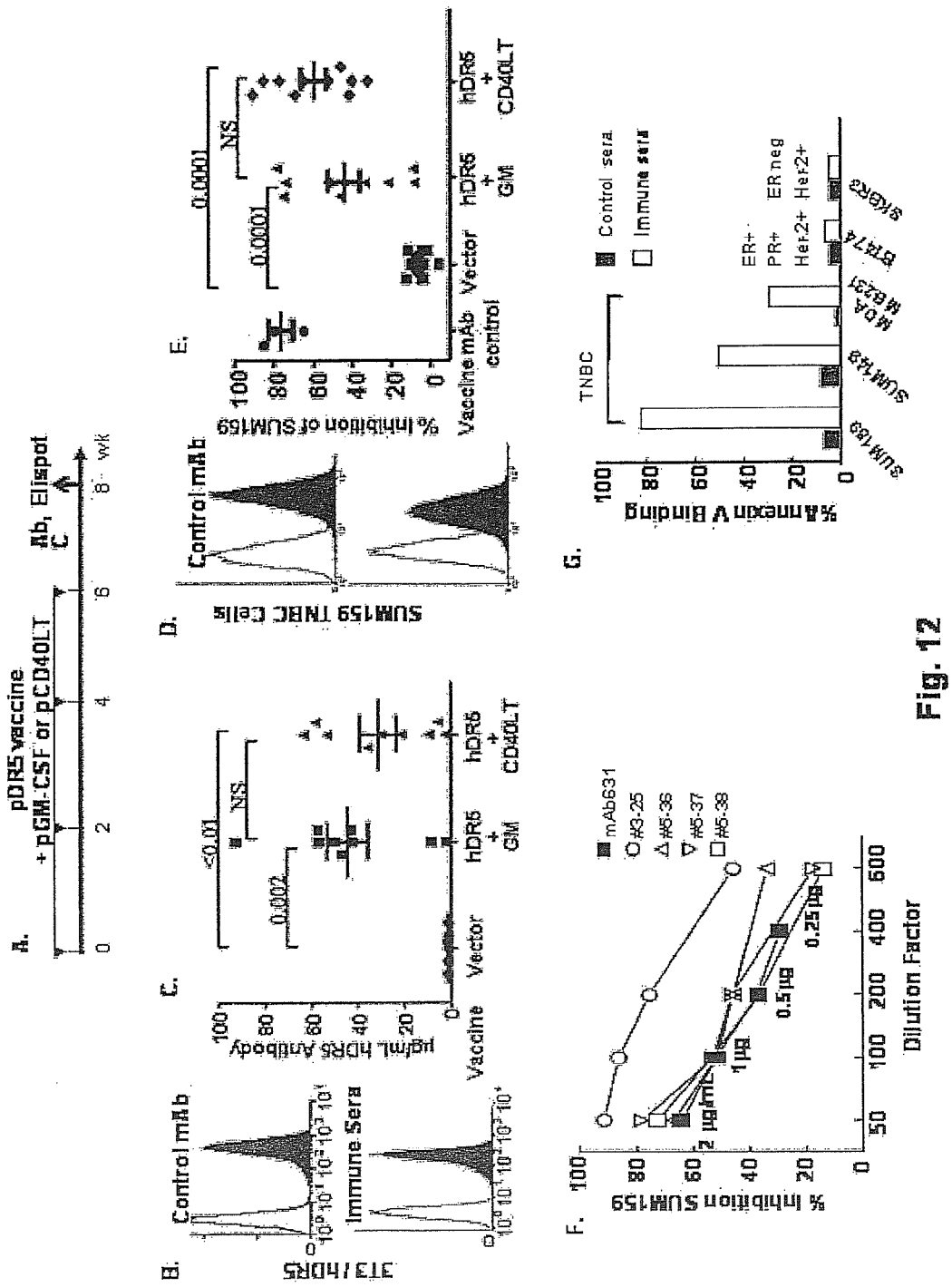
FIG. 12E shows a plot representing the growth inhibitory activity of 2% immune sera against SUM159 cells, as determined by MTT; "mAb control" condition represents known positive control anti-hDR5 mAb631 used at 1, 2, or 4 μg/ml.
FIG. 12F shows a titration graph of the growth inhibitory activity of individual immune sera as determined by MTT assay of SUM159 cells.
FIG. 12G shows a graph representing the apoptosis inducing activity of hDR5 immune sera against the triple negative breast cancer (TNBC) lines SUM159, SUM149, and MDAMB231 and the receptor positive lines BT474 and SKBR3.

To test the induction of hDR5 antibody, mice were electro-vaccinated four times at two week intervals with a plasmid encoding full length wild type human DR5 (pVAX-hDR5) and pGM-CSF or pCD40LT, according to the scheme of FIG. 12A. Sera were collected and analyzed by flow cytometry using mouse NIH3T3 cells stably transfected with hDR5 (3T3/hDR5, FIG. 12B). 3T3/hDR5 cells were recognized by a positive control hDR5 specific monoclonal antibody, HS201 (FIG. 12B, top panel, filled histogram) as well as hDR5 immune sera (FIG. 12B, bottom panel, filled histogram). The levels of hDR5 specific antibodies in the immune sera were determined by Elisa against recombinant human DR5 (aa 1-182). hDR5 ab levels were similar in mice co-vaccinated with GMCSF (44+27 µg/mL) and CD40LT (31+23 µg/mL) (FIG. 12C). We also determined that depletion of regulatory T cells, using anti-CD25 mAb did not significantly improve antibody titers, but reduced variation between animals (data not shown).

To test whether vaccination-induced anti-DR5 antibodies are agonistic or antagonistic in their activity, we measured their growth inhibitory and TRAIL-blocking activity on TNBC cell line SUM159. DR5 expression on SUM159 was verified by mAb HS201 and hDR5 immune sera (FIG. 12D, top and bottom panels, respectively). Using a MTT-based assay we observed significant inhibition of tumor cell growth with a 1:50 dilution of hDR5 immune sera, but not control sera (FIG. 12E). The level of tumor growth inhibition (FIG. 12E) correlated with antibody binding to hDR5 (FIG. 12C), indicating the activity of hDR5 antibodies. Immune sera at 0.2 to 2.0% (1:600-1:50) rendered 20-70% growth inhibition and this is directly comparable to the level of activity with 0.25 to 2 µg/mL of the agonist monoclonal antibody mAb631 (FIG. 12F), demonstrating the potency of immune sera, and indicating therapeutic levels of antibody in those sera. Non-specific toxicity imparted by the mouse sera is negligible at these low concentrations as demonstrated by sera from mice receiving blank vector pVAX1 (FIG. 12G, "control" bars). Immune sera had preferential activity in TNBC cells lines, SUM159, SUM149 and MDA-MB231 as compared to Her-2+ (SKBR3) and Her-2+/ER+ (BT474) (FIG. 12G). This is consistent with the reported pattern of differential sensitivity of TNBC lines to TRAIL, further confirming that immune serum induces apotptosis via agonistic action upon DR5.

hDR5 Immune Sera Induce Apoptosis Through the Extrinsic, Death Receptor Pathway

To determine the mechanism of antibody induced growth suppression, the effect of immune sera on SUM159 cells was compared with that of TRAIL and agonist monoclonal antibody mAb631 in Annexin V binding (FIG. 13A), morphological changes (FIG. 13B), and activation of caspase cleavage cascades involving caspase 8 (FIG. 13C). Treatment with hDR5 immune sera resulted in 70% annexin V positive cells (FIG. 13A). This coincided with the classical morphological attributes of apoptosis, membrane blebbing, cell shrinkage and nuclear condensation (FIG. 13B). Similar apoptotic activity was induced by 1 µg/mL TRAIL or 5 µg/mL of DR5 agonist mAb631. The small fraction of late apoptotic cells (9%) was similar to that seen in media control cultures (not shown). Therefore apoptosis in TNBC was induced by hDR5 immune sera. To test if the immune sera mediated cell death through a death receptor pathway, we tested the cleavage of caspase-3 and PARP (FIG. 13C) in the absence or presence of caspase-8 inhibitor (Z-IETD-FMK). Within 5 hours of treatment with immune sera caspase-3 cleavage was near completion (FIG. 13C, top panel, lane 3). Inhibition of caspase-8 with Z-IETD-FMK greatly reduced caspase-3 cleavage (lane 6). The level of reduction in caspase 3 cleavage by Z-IETD-FMK was comparable between the immune sera (lanes 3 vs. 6) and mAb631 (lanes 2 vs. 5) indicating similar role for caspase-8 in the apoptosis induced by immune sera and mAb631. Cleavage of PARP, which is further downstream of Caspase 3 was almost completely inhibited when either agent, hDR5 immune sera (FIG. 13C, middle panel, lanes 3 vs. 6) or DR5 agonist antibody (lanes 2 vs. 5) was used showing comparable signaling pathway for either treatment. Thus we conclude, that the same mechanism of apoptosis was induced by hDR5 immune sera and DR5 agonist, mAb631. To insure lack of activity of hDR5 immune sera on activated human T cells which also express DR5 on the cell surface, we tested for apoptosis and growth inhibition. Activated human T cells were verified to express detectable DR5 by single color flow cytometery (FIG. 13D, left panel). None of the DR5 agonists tested mAb631, TRAIL or hDR5 immune had any effect on activated T cell apoptosis or growth when compared to control cultures, as determined by Annexin V staining (FIG. 13D, middle panel. None of the agonists altered T cell growth as determined by Alamar Blue fluorescence (FIG. 13D, right panel). Thus, normal human T cells are resistant to hDR5 mediated apoptosis.

Apoptosis Signaling Induced by hDR5 Antisera is Mediated by hDR5-Specific IgG and is Amplified by Trail and by Crosslinking with an Anti-Ig.

We further tested whether bound anti-DR5 antibody interfered with TRAIL binding. Certain agonist monoclonal antibodies induce DR5 trimerization to initiate caspase-8 recruitment and cleavage. The activation of the caspase cascade has been shown to impair DR5 endocytosis (Austin et al., 2006), retaining DR5 on the cell surface for additional modulations and sustaining the death signal. SUM159 cells were incubated with 1% immune sera or nonimmune serum, washed and incubated with nonimmune goat IgG for a further 20 hours (Control in FIG. 14A). At 20 hours, less than 20% of immune serum treated cells were apoptotic, and only background apoptosis was seen in non-immune serum treated cells, as measured by Annexin V expression (FIG. 14A). When washed, antibody coated cells were incubated with TRAIL rather than control goat IgG (TRAIL, FIG. 14A), 67% of non-immune sera treated cells underwent apoptosis by 20 hours. In contrast, immune serum treated cells incubated with TRAIL were nearly 90% apoptotic (TRAIL in FIG. 14A). This indicates that not only do vaccine induced anti-DR5 antibodies not compete with TRAIL for binding to DR5; the antibodies actually cooperate with TRAIL to amplify DR5 death signaling. Apparently, TRAIL blocking or DR5 antagonist antibodies are largely absent from immune sera or are not induced by vaccination. This is in contrast to DR5 agonist Tra-8, which competes with TRAIL for the same binding site (Ichikawa et al., 2001), and ApoMab which overlaps with the TRAIL binding site (Adams et al., 2008). In separate studies, using DR4 and DR5 antagonists, we verified that TRAIL signals only through DR5, and that amplification of antisera agonist activity involves TRAIL binding to DR5 and not DR4 (not shown).

Crosslinking of the anti-DR5 IgGs by antibody or by Fc bearing cells has been shown to result in receptor clustering to amplify the DR5 signal (Adams et al., 2008) and cell apoptosis. When immune sera coated SUM159 cells were treated with anti-mouse IgG, apoptosis increased from 20% to >75% (FIG. 14A). These data indicate that when antibodies induced by anti-DR5 are crosslinked by anti-IgG, apoptosis signaling is amplified.

We also observed that, despite similar apparent hDR5 specific antibody concentration, some batches of immune sera obtained by pVAX-hDR5 vaccination had less direct apoptotic activity than others. We tested whether less potent immune sera could be similarly amplified through cross-linking. Batches of SUM159 cells were each treated with the immune serum of an individual mouse immunized with pVAX-hDR5. Each batch was then washed, divided in half, and further treated with either control goat IgG or goat anti-mouse IgG for 30 minutes. Although the immune sera alone demonstrated broad variability in apoptosis inducing power when administered alone ("Control" in FIG. 14(B), they were all amplified by cross-linking IgG to kill >80% of tumor cells ("α-IgG" in FIG. 14B). Thus similar epitopes may be recognized by immune sera but vary in their relative abundance in the polyclonal sera.

Taken together, the results of these experiments indicate that antiDR5-induced antibodies can have significantly amplified effects if the antibody coated target cells are encountered by Fc bearing cells, such as macrophages, or by endogenous TRAIL.

Induction of Agonist Antibodies and hDR5 Specific T Cell Responses by Three Different hDR5 DNA Vaccines.

When host cells are transfected to express full length wild type hDR5 during the vaccination process, the expressed DR5 may transducer death signals to provoke apoptosis of the host cells. In some cases it could be advantageous to prevent this apoptosis and extend the life of the host cells.

We therefore determined whether effective vaccination can be accomplished with expression vectors encoding forms of hDR5 with truncated or deleted intracellular death domains.

pVAX-hDR5 del (▲) has a premature stop codon in the death domain resulting from a 2 bp insertion at residue 1065 or aa 338 and the loss of 57 aa residues at the C-terminus. This variant has lost ~60-70% of its pro-apoptotic activity, although it retains most (aa 200-338) of the DR5 intracellular domain (Pai et al., 1998). The vaccine pVAX-hDR5 ECTM (ECTM) encodes the extracellular domain and transmembrane regions of hDR5, but without DR5 intracellular sequences.

To determine whether these constructs all induced effective expression and immunization, BALB/c mice were electrovaccinated 3 times with one of the above mentioned constructs in pVAX1 vector, or with control vector, along with pGMCSF (50 µg each plasmid DNA) (n=4-10). Immune sera (2%) was tested for growth inhibitory activity using SUM159 targets and MTT assay.

All constructs proved to induce stable proteins that were expressed on the surfaces of NIH3T3 cells and recognized by hDR5 specific mAb (FIG. 15A). When used as vaccines, all three constructs induced similar levels of hDR5 specific agonist antibodies were induced by phDR5, phDR5▲, and phDR5ectm, as determined by their growth inhibitory effect upon SUM159 cells (FIG. 15B). The mean+SE for inhibitory activity of immune sera was 58+6% (phDR5), 65+5% (phDR5▲) and 72+1% (phDR5ectm) compared to 36, 55 or 65% by 1, 2 or 4 µg/mL mAb63, respectively. Furthermore, all three constructs induced similar levels of γ-IFN secreting cells in response to an engineered antigen presenting cell that expressed the wild type full-length hDR5 (FIG. 15C).

In parallel, spleens were harvested from vaccinated animals and tested for hDR5 specific reactivity by ELIspot detection of γ-IFN production in response to antigen presenting cells (APC) engineered to express human DR5, MHC Kd and B7.1. APC expressing MHC Kd and B7.1 were used as control. Each vaccine was tested on 3-4 animals. The mean+SEM number of γ-IFN spots per 106 spleen cells were 593+57 (phDR5), 508+85 (phDR5▲) and 646+116 (phDR5ectm).

Taken together, the results of these experiments indicate that all three vaccines are effective at inducing a comprehensive hDR5-specific immune response.

EXAMPLE 4

Antibodies Induced by Vaccination with Anti-hDR5 Prevent the Growth of Human Breast Cancer Cells in SCID Mice
Tumor Growth in SCID Mice SUM159 cells were monodispersed in complete growth medium and treated with either a 20% final concentration of control or immune serum or a 20% final concentration of non-immune control serum spiked with agonist hDR5 monoclonal antibody mAb631 at a final concentration of 5 µg/mL. Cells were incubated at room temperature for 30 minutes with occasional agitation, washed twice with serum free media. Treated cells (3×106 in a 50 µL volume) were injected into the flanks of SCID mice, 8 mice per group. Animals were monitored weekly for tumor growth. Tumor volume was calculated as the product of the XY2 (X=long axis, Y=short axis). Log-rank (Mantel-Cox) test and Gehan-Breslow-Wilcoxon test was performed using GraphPad Prism version 5.01 for Windows, (GraphPad Software, San Diego, Calif.).

Results

SUM159 cells were pre-coated with either non-immune sera from mice vaccinated with control vector pVAX1, immune sera from mice vaccinated with pVAX-hDR5, or DR5 agonist monoclonal antibody mAb631, washed, and injected into the flanks of SCID mice at 3×106 per animal. Animals were monitored weekly for tumor growth for 14 weeks. Immune sera from hDR5 vaccinated mice protected >85% (6/7) mice from tumor growth. In contrast, treatment with the agonist mAb631 merely delayed tumor onset; 8/8 mice eventually developed tumor. The median time to tumor was 7 weeks for mAb631 compared to 3 weeks for control sera, but 8/8 mice eventually developed progressively growing tumors in both conditions (FIGS. 16A and B). Therefore, the polyclonal antibodies of hDR5 immune sera have potent tumor growth inhibitory activity in vivo that is superior to that of a monoclonal agonist antibody (p>0.0005).

Discussion

These experimental results represent the first description of a DNA-based vaccine strategy which employs the human death receptor DR5 as an antigen and that elicits potent DR5 agonist antibodies capable of direct binding to DR5 on human TNBC cells and induction of apoptosis. By inducing profound DR5 agonist antibodies, this vaccine can be used to prevent and treat triple-negative breast cancers which express DR5, and should also be widely applicable to other DR5 sensitive tumors including lung, colon, prostate, pancreas and ovary. In view of the predictive nature of the animal and cell models employed in these Examples, it is extremely likely that the present invention will be useful when applied in a clinical setting.

The results of these experiments also allay concerns that such a potent anti-DR5 immune response may have deleterious effects on immune effectors such as activated B cells and T cells which are known to express DR5. We have analyzed the effects of agonist antibodies and TRAIL on activated T cells and show they are resistant to apoptosis (FIG. 13D). Others have documented that upon activation, as cell surface DR5 expression increases, T cells and NK upregulate FLIP and XIAP, potent inhibitors of death receptor mediated apoptosis (Mirandola et al., 2004). Furthermore, there have been no reports from the clinical trials using death receptor agonist therapies including the various formulations of TRAIL and agonist antibodies specific for DR4 (HGS-ETR1, mapatumumab) and DR5 (HGS-ETR2, Lexatumumab) ApoMab and CS-1008 (Tra-8) that showed toxicity to lymphocytes.

In our studies coating SUM159 TNBC cells with immune sera prevented growth of >85% of tumors in SCID mice, whereas a defined monoclonal hDR5 agonist monoclonal antibody merely delayed tumor onset. Since cross-linking of antibody bound to tumor cells with anti-IgG greatly amplifies induction of apoptosis, the interaction of Fc bearing immune cells with antibody-coated tumor cells may be enhancing tumor destruction in vivo. Similarly, free or cell surface TRAIL ligand in the microenvironment can amplify tumor cell destruction by as it did in the experimental results shown in FIG. 14A. Tumor cell apoptosis, in turn, can initiate and continue to boost presentation of tumor antigens and thus further enhance antitumor response.

Since tumor specific apoptotic activity can be detected with less than 1% immune sera therapeutic levels of DR5 agonist antibodies were induced by vaccination. This level of circulating DR5 agonist antibodies has the potential to provide strong tumor inhibitory activity that can be further amplified by Fc or TRAIL bearing immune effectors.

There are numerous preclinical reports demonstrating that the anti-tumor effects of DR5 agonists can be greatly enhanced with conventional chemotherapeutic agents (Ding et al., 2002). Thus DR5 immunity can be used combined with traditional chemotherapeutic agents to provide an even greater impact on cancer control. This may broaden the scope of tumors that can be treated to include tumors with lower levels of intrinsic sensitivity to DR5 agonists and possibly reducing the necessary dose of chemotherapeutic agents.

REFERENCES CITED

Abhinandan K R, and Martin Martin, A C R. Analyzing the "Degree of Humanness" of Antibody Sequences. J. Mol. Biol. 2007; 369, 852-862.

Adams, C., Totpal, K., Lawrence, D., Marsters, S., Pitti, R., Yee, S., Ross, S., Deforge, L., Koeppen, H., Sagolla, M. et al. Structural and functional analysis of the interaction between the agonistic monoclonal antibody Apomab and the proapoptotic receptor DR5. Cell Death. Differ. 2008; 15:751-761

Ashkenazi A, Holland P, Eckhardt S G. Ligand-based targeting of apoptosis in cancer: the potential of recombinant human apoptosis ligand 2/Tumor necrosis factor-related apoptosis-inducing ligand (rhApo2L/TRAIL). J Clin Oncol 2008; 26:3621-30.

Austin, C. D., Lawrence, D. A., Peden, A. A., Varfolomeev, E. E., Totpal, K., De Maziere, A. M., Klumperman, J., Arnott, D., Pham, V., Scheller, R. H. et al. Death-receptor activation halts clathrin-dependent endocytosis. Proc. Natl. Acad. Sci. U.S.A. 2006; 103:10283-10288

Belyanskaya L L, Marti T M et al. Human agonistic TRAIL receptor antibodies Mapatumumab and Lexatumumab induce apoptosis in malignant mesothelioma and act synergistically with cisplatin. Molecular Cancer 2007, 6:66

Bolitho P, Voskoboinik I, Trapani J A, Smyth M J. Apoptosis induced by the lymphocyte effector molecule perforin. Curr Opin Immunol. 2007 June; 19(3):339-47.

Clancy L, Mruk K, Archer K, et al. Preligand assembly domain-mediated ligand-independent association between TRAIL receptor 4 (TR4) and TR2 regulates TRAIL-induced apoptosis. Proc Natl Acad Sci USA 2005; 102: 18099-18104

Colombo M P, Piconese S. Regulatory-T-cell inhibition versus depletion: the right choice in cancer immunotherapy. Nat Rev Cancer. 2007; 7:880-7.

Cranmer L D. and Hersh E. The Role of the CTLA4 Blockade in the Treatment of Malignant Melanoma. Cancer Invest. 2007; 25:7,613-631

Cretney E, Takeda K, Smyth M J. Cancer: Novel therapeutic strategies that exploit the TNF-related apoptosis-inducing ligand (TRAIL)/TRAIL receptor pathway. Int J Biochem Cell Biol 2007; 39:280-286.

Ding Z, Zhou J Y, Wei W Z, Baker V V, and Wu G S. Induction of apoptosis by the new anticancer drug XK469 in human ovarian cancer cell lines. Oncogene 2002; 21:4530-4538

Duiker E W, Mom C H, de J S, et al. The clinical trail of TRAIL. Eur J Cancer 2006; 42:2233-40.

Ghiringhelli, F, Menard C, Puig P E, et al. Metronomic cyclophosphamide regimen selectively depletes CD4+CD25+ regulatory T cells and restores T and NK effector functions in end stage cancer patients. Cancer Immunol. Immunother. 2007; 56: 641-648.

Guan B, Yue P, Clayman G L, et al. Evidence that the death receptor DR4 is a DNA damage-inducible, p53-regulated gene. Journal of Cellular Physiology 2001, 188:98-105

Hampton T. Novel targeted cancer drugs highlighted. JAMA 2006; 296:270.

Harrop R, John J, Carroll M W. Recombinant viral vectors: Cancer vaccines. Adv. Drug Deliv. Rev. 2006; 58: 931-947

Hotte S J, Hirte H W, Chen E X, et al. A phase 1 study of mapatumumab (monoclonal antibody to TRAIL-R1) in patients with advanced solid malignancies. Clin Cancer Res 2008; 14:3450-5

Ichikawa K, Liu W, Zhao L, Wang Z, Liu D, Ohtsuka T, Zhang H, Mountz J D, Koopman W J, Kimberly R P et al. Tumoricidal activity of a novel anti-human DR5 monoclonal antibody without hepatocyte cytotoxicity. Nature Medicine 2001; 7:954-960.

Jacob, J., Radkevich, O., Formi, G., Zielinski, J., Shim, D., Jones, R. F., and Wei, W. Activity of DNA vaccines encoding self or heterologous Her-2/neu in Her-2 or neu transgenic mice. Cellular Immunology 2006; 240:96-106.

Lin K Y, Guarnieri F G et al. Treatment of established tumors with a novel vaccine that enhances major histocompatibility class II presentation of tumor antigen. Cancer Res 1996; 56: 21-26.

Lucchini, F., Sacco, MG. et al. Early and multifocal tumors in breast, salivary, harderian and epididymal tissues developed in MMTY-Neu transgenic mice. Cancer Lett. 1992; 64: 203-209.

Mahoney K H., Miller B E., and Heppner, G. H. FACS quantitation of leucine aminopeptidase and acid phosphatase on tumor-associated macrophages from metastatic and non-metastatic mouse mammary tumors. J. Leukoc. Biol, 1985; 38: 573-585.

Martin-Orozco, Chen Dong C. Inhibitory costimulation and anti-tumor immunity. Semin. Cancer Biol. 2007; 17: 288-298.

Miller F, Jones R F. et al. From breast cancer immunobiology to her-2 DNA vaccine and autoimmune sequelae. Breast Dis. 2004; 20: 43-51.

Mirandola, P., Ponti, C., Gobbi, G., Sponzilli, I., Vaccarezza, M., Cocco, L., Zauli, G., Secchiero, P., Manzoli, F. A., and Vitale, M. Activated human NK and CD8+ T cells express both TNF-related apoptosis-inducing ligand (TRAIL) and TRAIL receptors but are resistant to TRAIL-mediated cytotoxicity. Blood 2004; 104:2418-2424.

Mocellin S, Rossi C R, Nitti D. Cancer vaccine development: on the way to break immune tolerance to malignant cells. Experimental Cell Research 299 (2004) 267-278.

Mosmann, T. Rapid colorimetric assay for cellular growth and survival: application to proliferation and cytotoxicity assays. J Immunol Methods 1983; 65:55-63.

Pai, S. I., Wu, G. S., Ozoren, N., Wu, L., Jen, J., Sidransky, D., and El-Deiry, W. S. Rare loss-of-function mutation of a death receptor gene in head and neck cancer. Cancer Res 1998; 58:3513-3518.

Panina-Bordignon P, Tan A, Termijtelen A, et al. Universally immunogenic T cell epitopes: promiscuous binding to human MHC class II and promiscuous recognition by T cells. Eur. J. Immunol. 1989; 19: 2237-2242.

Plummer R, Attard G. et al. Phase 1 and Pharmacokinetic Study of Lexatumumab in Patients with Advanced Cancers. Clin. Cancer Res. 2007; 13: 6187-6194

Rovero, S., Amici, A., et al. DNA vaccination against rat her-2/Neu p185 more effectively inhibits carcinogenesis than transplantable carcinomas in transgenic BALB/c mice. J. Immunol. 2000; 165: 5133-5142.

Rowinsky E K. Targeted induction of apoptosis in cancer management: the emerging role of tumor necrosis factor-related apoptosis-inducing ligand receptor activating agents. J Clin Oncol 2005; 23:9394-407.

Ramachandran A, Madesh M, Balasubramanian K A. Apoptosis in the intestinal epithelium: its relevance in normal and pathophysiological conditions. J Gastroenterol Hepatol. 2000 February; 15(2):109-20.

Rahman, M., Davis, S. R., Pumphrey, J. G., Bao, J., Nau, M. M., Meltzer, P. S., and Lipkowitz, S. TRAIL induces apoptosis in triple-negative breast cancer cells with a mesenchymal phenotype. Breast Cancer Res. Treat. 2008; 113: 217-230.

Sambrook J J. Molecular cloning: a laboratory manual. 3rd. Ed., 2001. Cold Spring Harbor Laboratory Press, Cold Spring Harbor, N.Y.

Sanderson K.; Scotland R.; Lee P.; et al. Autoimmunity in a phase I trial of a fully human anti-cytotoxic T-lymphocyte antigen-4 monoclonal antibody with multiple melanoma peptides and Montanide ISA 51 for patients with resected stages III and IV melanoma. J. Clin. Oncol. 2005; 23: 741-750.

Shi J, Zheng D, Liu Y, et al. Overexpression of soluble TRAIL induces apoptosis in human lung adenocarcinoma and inhibits growth of tumor xenografts in nude mice. Cancer Res 2005; 65:1687-92.

Smyth M J, Takeda K, Hayakawa Y, Peschon J J, van den Brink M R, Yagita H. Nature's TRAIL—on a path to cancer immunotherapy. Immunity. 2003 January; 18(1):1-6

Tolcher A W, Mita M. Phase I Pharmacokinetic and Biologic Correlative Study of Mapatumumab, a Fully Human Monoclonal Antibody With Agonist Activity to Tumor Necrosis Factor-Related Apoptosis-Inducing Ligand Receptor-. J. Clin Oncol 2007; 25:1390-1395.

Vassaux G, Nitcheu J, Jezzard S, Lemoine N R. Bacterial gene therapy strategies. J. Pathol. 2006; 208: 290-298.

Wassenaar T A, Quax W J, Mark A E. The conformation of the extracellular binding domain of Death Receptor 5 in the presence and absence of the activating ligand TRAIL: a molecular dynamics study. Proteins 2008; 70:333-43.

Wei, W. Z., Shi, W. P., Galy, A., Lichlyter, D., Hernandez, S., Groner, B., Heilbrun, L., and Jones, R. F. Protection against mammary tumor growth by vaccination with full-length, modified human ErbB-2 DNA. Int J Cancer 1999; 81:748-754.

Wei, W. Z., Jacob, J. B., Zielinski, J. F., Flynn, J. C., Shim, K. D., Alsharabi, G., Giraldo, A. A., and Kong, Y. M. Concurrent induction of antitumor immunity and autoimmune thyroiditis in CD4+ CD25+ regulatory T cell-depleted mice. Cancer Research 2005; 65:8471-8478.

Wei W-Z, Morris G P, Kong, Y-C. Anti-tumor immunity and autoimmunity: a balancing act of regulatory T cells. Cancer Immunol Immunother 2004; 53: 73-78.

Widen K, Mozaffari F et al. Overcoming immunosuppressive mechanisms. Ann. Oncol. 2008; 19 (Supplement 7): vii241-vii247.

Widera G, Austin M, et al. Increased DNA Vaccine Delivery and Immunogenicity by electroporation In Vivo. J. Immunol. 2000, 164: 4635-4640.

Wu G S, Burns T F, Zhan Y, Alnemri E S, El-Deiry W S. Molecular cloning and functional analysis of the mouse homologue of the KILLER/DR5 tumor necrosis factor-related apoptosis-inducing ligand (TRAIL) death receptor. Cancer Res 1999; 59:2770-5.

---

The invention claimed is:

1. A vaccine for inducing agonist antibodies in a mammalian subject against the cellular death receptor DR5 expressed by target cells of the mammalian subject, said vaccine comprising an effective amount of a naked DNA expression vector including an isolated nucleic acid sequence encoding an antigenic fusion polypeptide consisting of the extracellular (ec) domain of DR5 fused to the transmembrane (tm) domain of DR5, and a nontoxic fragment of tetanus toxin fused to said tm domain, wherein said ec and tm domains are selected from the group consisting of the ec and tm domains of murine DR5 and the ec and tm domains of human DR5, and said nontoxic fragment of tetanus toxin consists of toxin fragment C domain 1 (td1), wherein said expression vector induces the expression of said antigenic fusion polypeptide in the mammalian subject, wherein said agonist antibodies induced in response to said vaccine agonize DR5 expressed by the target cells of the mammalian subject, to trigger apoptosis in the target cells, and said vaccine further including an effective amount of granulocyte macrophage colony stimulating factor (GM-CSF) as an adjuvant.

2. The vaccine of claim 1, wherein the mammalian subject is human.

3. The vaccine of claim 1, wherein the target cells are tumor cells.

4. The vaccine of claim 3, wherein the tumor cells are solid tumor cells.

5. The vaccine of claim 4 wherein the solid tumor cells are mammary tumor cells.

6. The vaccine of claim 4 wherein the solid tumor cells are selected from the group consisting of colorectal, ovarian, breast, non-small cell lung, prostate, pancreatic, head and neck, and skin cancers.

7. The vaccine of claim 3 wherein the tumor cells are hematopoietic tumor cells.

8. The vaccine of claim 1, wherein said GM-CSF is delivered to the mammalian subject as an expression vector comprising a polynucleotide encoding GM-CSF, said expression vector being suitable for expression of said polynucleotide in the mammalian subject.

9. The vaccine of claim 1, wherein said GM-CSF is delivered to the mammalian subject as GM-CSF protein.

10. The vaccine according to claim 1, wherein said ec domain of murine DR5 consists of a polypeptide consisting of SEQ ID NO: 2, said tm domain consists of a polypeptide consisting of SEQ ID NO: 4, said ec domain of human DR5 consists of a polypeptide consisting of SEQ ID NO: 6, and said tm domain of human DR5 consists of a polypeptide consisting of SEQ ID NO: 8.

* * * * *

UNITED STATES PATENT AND TRADEMARK OFFICE
CERTIFICATE OF CORRECTION

| | |
|---|---|
| PATENT NO. | : 8,685,939 B2 |
| APPLICATION NO. | : 13/128046 |
| DATED | : April 1, 2014 |
| INVENTOR(S) | : Wei-Zen Wei et al. |

It is certified that error appears in the above-identified patent and that said Letters Patent is hereby corrected as shown below:

In the Specification

Column 1, Lines 11-14 (approx.), should read, This invention was made with government support under Contract CA076340 awarded by the National Institutes of Health and Contract W81XWH-07-1-0521 awarded by Army Medical Research and Material Command. The government has certain rights in the invention.

Signed and Sealed this
Twenty-third Day of May, 2017

Michelle K. Lee
*Director of the United States Patent and Trademark Office*